US010548989B2

(12) United States Patent
Bradbury et al.

(10) Patent No.: US 10,548,989 B2
(45) Date of Patent: Feb. 4, 2020

(54) NANOPARTICLE IMMUNOCONJUGATES

(71) Applicants: Memorial Sloan Kettering Cancer Center, New York, NY (US); Cornell University, Ithaca, NY (US); The Curators of the University of Missouri, Columbia, MO (US)

(72) Inventors: Michelle S. Bradbury, New York, NY (US); Thomas P. Quinn, Columbia, MO (US); Feng Chen, New York, NY (US); Barney Yoo, New York, NY (US); Jason Lewis, New York, NY (US); Ulrich Wiesner, Ithaca, NY (US); Kai Ma, Ithaca, NY (US)

(73) Assignees: Memorial Sloan Kettering Cancer Center, New York, NY (US); Cornell University, Ithaca, NY (US); The Curators of the University of Missouri, Columbia, MO (US)

( * ) Notice: Subject to any disclaimer, the term of this patent is extended or adjusted under 35 U.S.C. 154(b) by 0 days.

(21) Appl. No.: 15/564,315

(22) PCT Filed: Apr. 7, 2016

(86) PCT No.: PCT/US2016/026434
§ 371 (c)(1),
(2) Date: Oct. 4, 2017

(87) PCT Pub. No.: WO2016/164578
PCT Pub. Date: Oct. 13, 2016

(65) Prior Publication Data
US 2018/0133342 A1 May 17, 2018

Related U.S. Application Data

(60) Provisional application No. 62/144,278, filed on Apr. 7, 2015, provisional application No. 62/151,943, filed on Apr. 23, 2015.

(51) Int. Cl.
| | |
|---|---|
| *A61K 47/69* | (2017.01) |
| *A61K 51/10* | (2006.01) |
| *A61K 47/65* | (2017.01) |
| *A61K 47/60* | (2017.01) |
| *A61K 51/12* | (2006.01) |
| *A61K 45/06* | (2006.01) |
| *A61K 49/00* | (2006.01) |
| *A61K 49/18* | (2006.01) |
| *C07K 16/40* | (2006.01) |

(52) U.S. Cl.
CPC .......... *A61K 47/6923* (2017.08); *A61K 45/06* (2013.01); *A61K 49/0058* (2013.01); *A61K 49/1824* (2013.01); *A61K 51/1093* (2013.01); *A61K 51/1251* (2013.01); *C07K 16/40* (2013.01); *C07K 2317/55* (2013.01); *C07K 2317/569* (2013.01); *C07K 2317/622* (2013.01)

(58) Field of Classification Search
CPC ............ A61K 47/6923; A61K 51/1093; A61K 49/1824; A61K 49/0058; A61K 51/1251; A61K 51/10; A61K 51/0478; A61K 49/0093; A61K 47/65; A61K 47/60; A61K 51/1244; C07K 2317/622
See application file for complete search history.

(56) References Cited

U.S. PATENT DOCUMENTS

| | | |
|---|---|---|
| 4,680,338 A | 7/1987 | Sundoro |
| 5,122,368 A | 6/1992 | Greenfield et al. |
| 5,141,648 A | 8/1992 | Hylarides et al. |
| 5,208,020 A | 5/1993 | Chari et al. |
| 5,416,064 A | 5/1995 | Chari et al. |
| 5,475,092 A | 12/1995 | Chari et al. |
| 5,543,390 A | 8/1996 | Yatvin et al. |
| 5,563,250 A | 10/1996 | Hylarides et al. |
| 5,585,499 A | 12/1996 | Chari et al. |
| 5,880,270 A | 3/1999 | Berninger et al. |
| 6,214,345 B1 | 4/2001 | Firestone et al. |
| 6,340,701 B1 | 1/2002 | Chari et al. |
| 6,372,738 B2 | 4/2002 | Chari et al. |
| 6,436,931 B1 | 8/2002 | Chari et al. |
| 6,989,452 B2 | 1/2006 | Ng et al. |
| 7,129,261 B2 | 10/2006 | Ng et al. |
| 7,375,078 B2 | 5/2008 | Feng |
| 7,498,302 B2 | 3/2009 | Ng et al. |
| 7,507,420 B2 | 3/2009 | Ng et al. |

(Continued)

FOREIGN PATENT DOCUMENTS

| | | |
|---|---|---|
| WO | WO-2014/145606 A1 | 9/2014 |
| WO | WO-2016/164578 A1 | 10/2016 |

OTHER PUBLICATIONS

Rudikoff et al., Proc Natl Acad Sci USA 79: 1979-1983 (Year: 1982).*

(Continued)

*Primary Examiner* — Phuong Huynh
(74) *Attorney, Agent, or Firm* — Choate, Hall & Stewart LLP; William R. Haulbrook; Margo R. Monroe

(57) ABSTRACT

Disclosed herein are nanoparticle immunoconjugates useful for therapeutics and/or diagnostics. The immunoconjugates have diameter (e.g., average diameter) no greater than 20 nanometers (e.g., as measured by dynamic light scattering (DLS) in aqueous solution, e.g., saline solution). In certain embodiments, the conjugates are silica-based nanoparticles with single chain antibody fragments attached thereto.

20 Claims, 9 Drawing Sheets

(56) References Cited

U.S. PATENT DOCUMENTS

| | | | |
|---|---|---|---|
| 7,691,962 B2* | 4/2010 | Boyd | B82Y 30/00 |
| | | | 530/300 |
| 7,910,594 B2 | 3/2011 | Vlahov et al. | |
| 7,968,586 B2 | 6/2011 | Gangwar et al. | |
| 7,989,434 B2 | 8/2011 | Feng | |
| 7,994,135 B2 | 8/2011 | Doronina et al. | |
| 7,999,083 B2 | 8/2011 | Govindan et al. | |
| 8,153,768 B2 | 4/2012 | Kunz et al. | |
| 8,236,319 B2 | 8/2012 | Chari et al. | |
| 8,298,677 B2 | 10/2012 | Wiesner et al. | |
| 2004/0101822 A1* | 5/2004 | Wiesner | B82Y 30/00 |
| | | | 435/5 |
| 2006/0222595 A1* | 10/2006 | Mukherjee | A61K 39/44 |
| | | | 424/9.34 |
| 2008/0317768 A1* | 12/2008 | Bianchi | A61K 33/06 |
| | | | 424/179.1 |
| 2010/0183504 A1* | 7/2010 | Chen | A61K 49/0002 |
| | | | 424/1.29 |
| 2013/0039848 A1 | 2/2013 | Bradbury et al. | |
| 2014/0248210 A1 | 9/2014 | Bradbury et al. | |

OTHER PUBLICATIONS

Casset et al., Biochemical and Biophysical Research Communications 307:198-205 (Year: 2003).*
Vajdos et al., Journal of Molecular biology 320: 415-428 (Year: 2002).*
Holm et al., Molecular Immunology 44: 1075-1084 (Year: 2007).*
Chen et al., Journal of Molecular Biology 293: 865-881 (Year: 1999).*
Wu et al., Journal of Molecular Biology 294: 151-162 (Year: 1999).*
Yu et al., Investigative Ophthalmology & Visual Science 49(2): 522-527 (Year: 2008).*
Jubala et al., Vet Pathol 42: 468-476 (Year: 2005).*
Nelson et al., Nature Biotechnology 27(4): 331-337 (Year: 2009).*
Benezra, M. et al., Ultrasmall Integrin-Targeted Silica Nanoparticles Modulate Signaling Events and Cellular Processes in a Concentration-Dependent Manner, Small, 11(14):1721-1732 (2015).
Detappe, A. et al., Advanced multimodal nanoparticles delay tumor progression with clinical radiation therapy, Journal of Controlled Release, 238:103-113 (2016).
Doronina, S. et al., Enahnced Activity of Monomethylauristatin F through Monoclonal Antibody Delivery: Effects of Linker Technology on Efficacy and Toxicity, Bioconjug Chem, 17:114-124 (2006).
Hamann, P. et al., An Anti-MUC1 Antibody-Calicheamicin Conjugate for Treatment of Solid Tumors. Choice of Linker and Overcoming Drug Resistance, Bioconjug Chem, 16:346-353 (2005).
International Search Report, PCT/US2016/026434, 5 pages, dated Jul. 4, 2016.
Lee, K. M. et al., X-Ray Crystal Structure and Binding Mode Analysis of Human S-Adenosylhomocysteine Hydrolase Complexed with Novel Mechanism-based Inhibitors, Haloneplanocin A Analogues, J. Med. Chem., 54:930-938 (2011).
Wilks, M. Q. et al., Imaging PEG-Like Nanoprobes in Tumor, Transient Ischemia, and Inflammatory Disease Models, Bioconjugate Chemistry, 26(6):1061-1069 (2015).
Written Opinion, PCT/US2016/026434, 8 pages, dated Jul. 4, 2016.
Yoo, B. et al., Ultrasmall dual-modality silica nanoparticle drug conjugates: Design, synthesis, and characterization, Bioorganic & Medicinal Chemistry, 23(22):7119-7130, (2015).

* cited by examiner

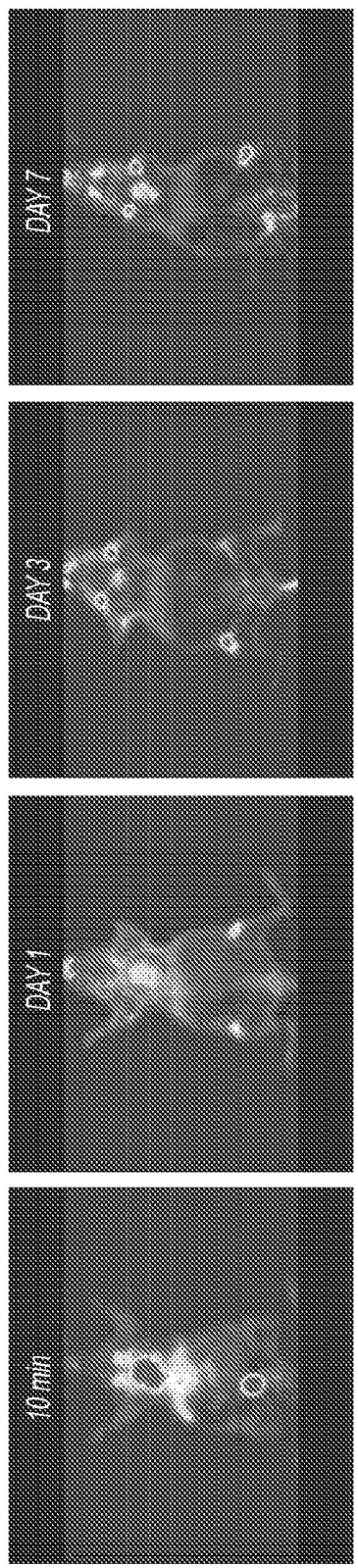
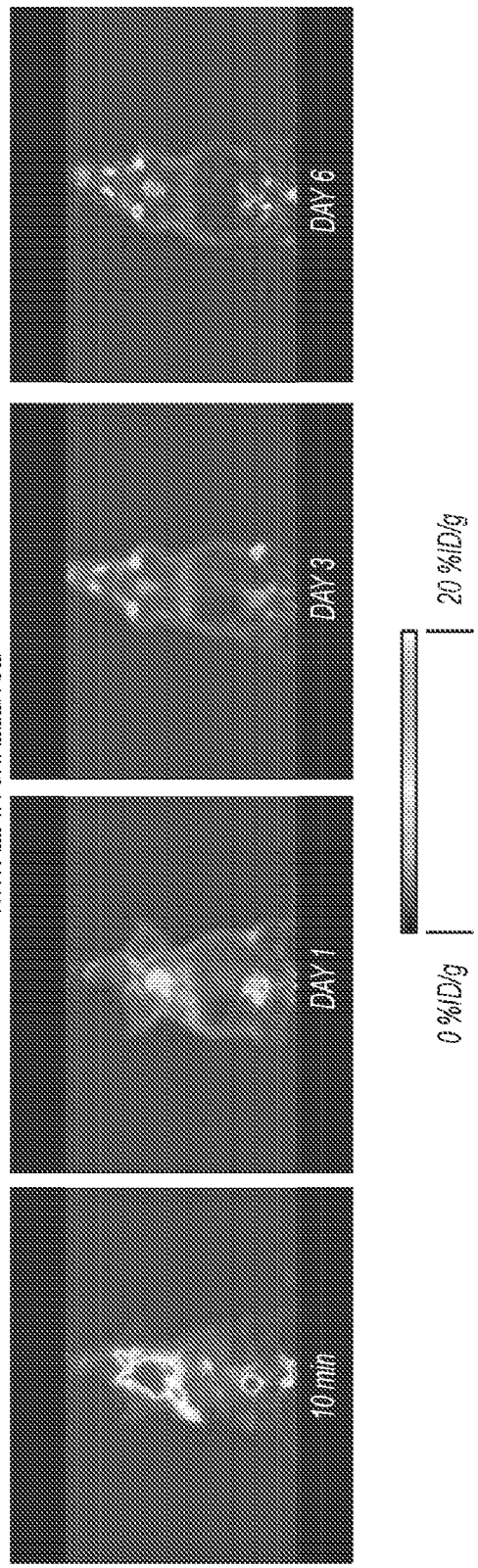
FIG. 5A WITHOUT EDTA CHALLENGE
FIG. 5B WITH EDTA CHALLENGE

SCHEME 1. THIOL-MALEIMIDE CHEMISTRY

SCHEME 2. ALKENE-TETRAZINE CHEMISTRY

NANOPARTICLE IMMUNOCONJUGATES

CROSS REFERENCE TO RELATED APPLICATION

This application is the U.S. National Stage Entry of International Application No. PCT/US16/26434 filed Apr. 7, 2016, which claims the benefit of U.S. Application Ser. No. 62/144,278 filed on Apr. 7, 2015 and U.S. Application Ser. No. 62/151,943 filed on Apr. 23, 2015, the disclosures of which are hereby incorporated by reference in their entireties.

GOVERNMENT FUNDING

This invention was made with government support under grant number CA199081 awarded by National Institutes of Health. The government has certain rights in the invention.

FIELD OF THE INVENTION

This invention relates generally to nanoparticle immunoconjugates (e.g., under 20 nanometers in diameter), useful, for example, for the detection, prevention, and/or treatment of cancer and other diseases.

BACKGROUND

Nano-therapeutic and/or -diagnostic delivery vehicles are typically macro- or supra-molecular multicomponent systems, ranging in size from 1-1,000 nm, that are either inherently therapeutic (e.g., no active pharmaceutical ingredient) or function as therapeutic or diagnostic delivery systems. To date, liposomal nanoparticles and biologics comprise a large proportion of the number of FDA-approved products or products in clinical trials used to treat and/or detect a variety of cancer types, while a number of polymer-based particle formulations are currently in early phase trials.

Desirable candidates for nanotherapeutic delivery systems share a common feature of incorporating and releasing a drug compound in a controlled manner, which can favorably alter drug bioavailability and pharmacokinetics, while minimizing off-target toxicities. Ideally, an imaging label is incorporated therein to assess their precise localization and retention at disease sites.

However, these systems function using different mechanisms. For example, antibody drug conjugates (ADCs) achieve lower drug toxicity primarily through active targeting of tumor cells and conditional release of drug molecules. Upon binding a cell surface antigen, active drug release occurs after cellular internalization and endosomal uptake. On the other hand, liposomes and polymer-based drug delivery systems, which are typically much larger assembled complexes (~20-150 nm diameters) passively loaded with a greater payload (~10,000 drug molecules for Doxil) or imaging agents, have generally lacked targeting capabilities (BIND-014 is an exception). Therefore, these complexes rely primarily on the well-known enhanced permeability and retention (EPR) effect for the successful delivery of nano-formulated drugs. While interstitial permeation of liposomes may be poor due to their size, the free drug is released through various mechanisms that are not entirely understood. For example, Abraxane (~140 nm) relies on a different approach to enhance the bioavailability of a hydrophobic compound. In this case, a specific formulation of albumin and drug (paclitaxel) forms the initial complex, which is in turn estimated to disperse into smaller protein-drug aggregates upon injection.

Metastatic disease may effectively be treated with immunotherapies; however, a significant subpopulation will not respond due to lack of antigenic mutations or the immune-evasive properties of cancer. In addition, although radiation therapy (RT) is a standard treatment for cancer, local failures occur. Preclinical data indicate that RT can potentiate the systemic efficacy of immunotherapy, while activation of the innate and adaptive immune system can enhance the local efficacy of RT.

There remains a need for a platform that can be used for the detection, prevention, and/or treatment of cancer and other diseases.

SUMMARY

Described herein are target-specific nanoparticle immunoconjugates (e.g., single chain antibody fragments bound to the particle surface) for targeted diagnostic and/or therapeutic platforms. In certain embodiments, the nanoparticle immunoconjugates are less than 20 nm (e.g., 6 to 10 nm) in diameter. This small size is found to offer advantages in therapeutic and/or imaging applications. For example, the disclosed immunoconjugates may offer improved targeting of diseased tissue and reduced non-specific uptake by organs (e.g., by the liver). The smaller immunoconjugates may also demonstrate reduced immune reactivity, thereby further improving efficacy.

Also described herein is a multi-therapeutic platform that comprises an immunoconjugate and therapeutic radioisotopes. In certain embodiments, immunoconjugates and therapeutic radioisotopes are delivered in concert for synergistic effects of combined radiation therapy and immunotherapy. In certain embodiments, an antibody fragment and a therapeutic radioisotope are attached to nanoparticles, thereby creating a target-specific nanoparticle immunoconjugate. A given nanoparticle can have both radionuclides (radioisotopes) and antibodies (and/or antibody fragments) attached thereto (in which case, the immunoconjugate is a radioimmunoconjugate). Also, in some embodiments, a portion of the administered nanoparticles have radionuclides attached (covalently or non-covalently bonded, or otherwise associated with the nanoparticle) while other administered nanoparticles have antibody fragments attached. Also included in various embodiments are combination therapies in which either exiting (e.g., traditional) radiotherapy is combined with administration of nanoparticle immunoconjugates described herein, or existing (e.g., traditional) immunotherapy is combined with administration of nanoparticle radioconjugates (nanoparticles with bound radioisotopes), The certain embodiments, the target-specific nanoparticle immunoconjugates comprise a targeting peptide. In certain embodiments, the therapeutic radioisotope is delivered separately from the target-specific nanoparticle immunoconjugate (e.g., via radiation therapy or via attached to a separate target-specific nanoparticle). In certain embodiments, immunotherapy is delivered separately from the target-specific immunoconjugate. In certain embodiments, an antibody fragment is attached to one polyethylene glycol (PEG) moiety (via a particular chelator) and a radioisotope is attached to another PEG moiety (via another chelator). The PEG moieties are then attached to nanoparticles.

In one aspect, the invention is directed to An immunoconjugate comprising: a nanoparticle; and an antibody fragment conjugated to the nanoparticle, wherein the nanoparticle has a diameter (e.g., average diameter) no greater than 20 nanometers (e.g., as measured by dynamic light scattering (DLS) in aqueous solution, e.g., saline solution) (e.g., wherein the average nanoparticle diameter is from 1 to 20 nm, e.g., from 1 to 15 nm, e.g., from 1 to 10 nm, e.g., from 1 to 8 nm, e.g., from 4 to 10 nm, e.g., from 4 to 8 nm) (e.g., wherein the immunoconjugate has an average diameter no greater than 50 nm, e.g., no greater than 40 nm, e.g., no greater than 30 nm, e.g., no greater than 20 nm, e.g., no greater than 15 nm, e.g., no greater than 10 nm).

In certain embodiments, the antibody fragment is covalently or non-covalently bonded to the nanoparticle via a linker or covalently or non-covalently bonded directly to the nanoparticle, or associated with the nanoparticle or a composition surrounding the nanoparticle, e.g., via van der Waals forces.

In certain embodiments, the nanoparticle is coated with an organic polymer (e.g., polyethylene glycol (PEG)) (e.g., wherein immunoconjugate comprises a chelator).

In certain embodiments, a targeting peptide (e.g., alphaMSH, any peptide known to be immunomodulatory and anti-inflammatory in nature).

In certain embodiments, the antibody fragment is in a range from about 5 kDa to about 25 kDa (e.g., from about 10 kDa to about 20 kDa, e.g., about 15 kDa) (e.g., wherein the antibody fragment comprises a functional single domain antibody fragment).

In certain embodiments, the antibody fragment is from about 20 kDa to about 45 kDa (e.g., from about 25 kDa to about 30 kDa) (e.g., wherein the antibody fragment comprises a functional single chain antibody fragment).

In certain embodiments, the antibody fragment is from about 40 kDa to about 80 kDa (e.g., from about 50 kDa to about 70 kDa, e.g., about 60 kDa) (e.g., wherein the antibody fragment comprises a functional fab fragment).

In certain embodiments, the nanoparticle comprises silica.

In certain embodiments, the nanoparticle comprises a silica-based core and a silica shell surrounding at least a portion of the core.

In certain embodiments, the nanoparticle comprises a fluorescent compound within the core.

In certain embodiments, the antibody fragment is a member selected from the set consisting of a recombinant antibody fragment (fAbs), a single chain variable fragment (scFv), and a single domain antibody (sdAb) fragment.

In certain embodiments, the antibody fragment is a single chain variable fragment (scFv).

In certain embodiments, the antibody fragment is a single domain (sdAb) fragment.

In certain embodiments, the nanoparticle (a single nanoparticle) has from one to ten antibody fragments (e.g., from 1 to 7, e.g., from 1 to 5, e.g., from 2 to 7, e.g., from 2 to 5, e.g., from 1 to 4, e.g., from 2 to 4) attached thereto.

In certain embodiments, the antibody fragment is conjugated to the nanoparticle via a PEG moiety and a chelator.

In certain embodiments, the nanoparticle has a diameter (e.g., average diameter) no greater than 15 nanometers (e.g., no greater than 13 nanometers, e.g., no greater than 10 nanometers).

In certain embodiments, the nanoparticle has a diameter (e.g., average diameter) in a range from 1 nm to 20 nm (e.g., from 2 nm to 15 nm, e.g., from 5 nm to 15 nm, e.g., from 1 nm to 10 nm, e.g., from 2 nm to 10 nm, e.g., from 5 nm to 10 nm).

In certain embodiments, the antibody fragment comprises a member selected from the set consisting of anti-CEA scFv, anti-GPIIb/IIIa, anti-VEGF-A, and anti-TNF-α (e.g., PEGylated).

In certain embodiments, the immunoconjugate comprises one or more imaging agents (e.g., within the nanoparticle, attached to the nanoparticle, and/or attached to the antibody fragment).

In certain embodiments, the one or more imaging agents comprise a PET tracer (e.g., $^{89}$Zr, $^{64}$Cu, and/or [$^{18}$F] fluorodeoxyglucose).

In certain embodiments, the one or more imaging agents comprise a fluorophore (e.g., a cyanine).

In certain embodiments, the immunoconjugate further comprises a therapeutic agent (e.g., wherein the therapeutic agent is attached to the nanoparticle, or to the antibody fragment, or to both the nanoparticle and the antibody fragment, e.g., wherein the attachment is covalent or non-covalent).

In certain embodiments, the therapeutic agent comprises a chemotherapy drug (e.g., sorafenib, paclitaxel, docetaxel, MEK162, etoposide, lapatinib, nilotinib, crizotinib, fulvestrant, vemurafenib, bexorotene, and/or camptotecin).

In certain embodiments, the therapeutic agent comprises a radioisotope (e.g., wherein the radioisotope is attached to the nanoparticle via a second chelator) (e.g., wherein the radioisotope is a therapeutic radioisotope).

In certain embodiments, the radioisotope is a member selected from the group consisting of $^{99m}$Tc, $^{111}$In, $^{64}$Cu, $^{67}$Ga, $^{186}$Re, $^{188}$Re, $^{153}$Sm, $^{177}$Lu, $^{67}$Cu, $^{123}$I, $^{124}$I, $^{125}$I, $^{11}$C, $^{13}$N, $^{15}$O, $^{18}$F, $^{186}$Re, $^{188}$Re, $^{153}$Sm, $^{166}$Ho, $^{177}$Lu, $^{149}$Pm, $^{90}$Y, $^{213}$Bi, $^{103}$Pd, $^{109}$Pd, $^{159}$Gd, $^{140}$La, $^{198}$Au, $^{199}$Au, $^{169}$Yb, $^{175}$Yb, $^{165}$Dy, $^{166}$Dy, $^{67}$Cu, $^{105}$Rh, $^{111}$Ag, $^{89}$Zr, $^{225}$Ac, and $^{192}$Ir.

In another aspect, the invention is directed to a method of treating a disease or condition, the method comprising administering to a subject a pharmaceutical composition comprising the immunoconjugate (e.g., to target a particular type of tissue, e.g., cancer).

In certain embodiments, the method comprises administering a therapeutic radioisotope (e.g., wherein the therapeutic radioisotope is attached to a second nanoparticle having a diameter (e.g., average diameter) no greater than 20 nanometers (e.g., as measured by dynamic light scattering (DLS) in aqueous solution, e.g., saline solution) (e.g., wherein the radioisotope is attached to the second nanoparticle via a second chelator)) (e.g., wherein the second nanoparticle has a diameter from 1 to 20 nm, e.g., from 1 to 15 nm, e.g., from 1 to 10 nm, e.g., from 1 to 8 nm, e.g., from 4 to 10 nm, e.g., from 4 to 8 nm).

In another aspect, the invention is directed to a method of treating a disease or condition, the method comprising administering to a subject a pharmaceutical composition comprising the immunoconjugate (e.g., to target a particular type of tissue, e.g., cancer) (e.g., for combined radiation therapy and immunotherapy).

In certain embodiments, the pharmaceutical composition further comprises a carrier.

In another aspect, the invention is directed to a method of in vivo imaging (e.g., intraoperative imaging), the method comprising: administering to a subject a composition comprising the immunoconjugate (e.g., such that the immunoconjugate preferentially collects in a particular region, e.g., near or within a particular tissue type, e.g., cancer), wherein the immunoconjugate comprises an imaging agent; and detecting (e.g., via PET, X-ray, MRI, CT, etc.) the imaging agent.

In another aspect, the invention is directed to a method of making the immunoconjugate, the method comprising: contacting a nanoparticle-PEG-thiol with a protein-maleimide, thereby producing the immunoconjugate.

In certain embodiments, the method further comprises reacting the nanoparticle with one or more compounds, the one or more compounds comprising a thiol moiety and an amine moiety (e.g., cysteine methyl ester or cysteamine-HCl), thereby producing a nanoparticle-PEG-amine; reacting the nanoparticle-PEG-amine with SPDP, then removing a pyridine 2-thione from the product (e.g., using TCEP), thereby producing the nanoparticle-PEG-thiol.

In another aspect, the invention is directed to a method of making the immunoconjugate, the method comprising: modifying the antibody fragment (protein) with a first click reactive group (e.g., methyltetrazine-PEG4-NHS ester; modifying a nanoparticle-PEG-amine with a click partner of the first click reactive group (e.g., TCO-PEG4-NHS ester); and reacting the modified antibody fragment with the modified nanoparticle-PEG, thereby producing the immunoconjugate.

In certain embodiments, the method further comprises reacting the nanoparticle with one or more compounds, the one or more compounds comprising a thiol moiety and an amine moiety (e.g., cysteine methyl ester or cysteamine-HCl), thereby producing the nanoparticle-PEG-amine.

In another aspect, the invention is directed to a method of treating a disease or condition, the method comprising administering to a subject a composition (e.g., a pharmaceutical composition) comprising: a nanoparticle; and a therapeutic radioisotope conjugated to the nanoparticle (e.g., covalently or non-covalently bonded to the nanoparticle via a linker or covalently or non-covalently bonded directly to the nanoparticle, or associated with the nanoparticle or a composition surrounding the nanoparticle, e.g., via van der Waals forces), wherein the nanoparticle has a diameter (e.g., average diameter) no greater than 20 nanometers (e.g., as measured by dynamic light scattering (DLS) in aqueous solution, e.g., saline solution) (e.g., wherein the average nanoparticle diameter is from 1 to 20 nm, e.g., from 1 to 15 nm, e.g., from 1 to 10 nm, e.g., from 1 to 8 nm, e.g., from 4 to 10 nm, e.g., from 4 to 8 nm) (e.g., to target a particular type of tissue, e.g., cancer).

In certain embodiments, the method comprises administering immunotherapy (e.g., wherein the immunotherapy comprises administering to a subject a pharmaceutical composition comprising the immunoconjugate).

In another aspect, the invention is directed to an immunoconjugate comprising: a nanoparticle; and an antibody fragment conjugated to the nanoparticle (e.g., covalently or non-covalently bonded to the nanoparticle via a linker or covalently or non-covalently bonded directly to the nanoparticle, or associated with the nanoparticle or a composition surrounding the nanoparticle, e.g., via van der Waals forces), wherein the nanoparticle has a diameter (e.g., average diameter) no greater than 20 nanometers (e.g., as measured by dynamic light scattering (DLS) in aqueous solution, e.g., saline solution) (e.g., wherein the average nanoparticle diameter is from 1 to 20 nm, e.g., from 1 to 15 nm, e.g., from 1 to 10 nm, e.g., from 1 to 8 nm, e.g., from 4 to 10 nm, e.g., from 4 to 8 nm) (e.g., wherein the immunoconjugate has an average diameter no greater than 50 nm, e.g., no greater than 40 nm, e.g., no greater than 30 nm, e.g., no greater than 20 nm, e.g., no greater than 15 nm, e.g., no greater than 10 nm) (e.g., wherein the nanoparticle is coated with an organic polymer (e.g., polyethylene glycol (PEG)) (e.g., wherein immunoconjugate comprises a chelator), for use in a method of treating a disease or condition in a subject, wherein the treating comprises: delivering the immunoconjugate to the subject; and delivering a therapeutic radioisotope (e.g., wherein the therapeutic radioisotope is attached to a second nanoparticle having a diameter (e.g., average diameter) no greater than 20 nanometers (e.g., as measured by dynamic light scattering (DLS) in aqueous solution, e.g., saline solution) (e.g., wherein the radioisotope is attached to the second nanoparticle via a second chelator)).

In another aspect, the invention is directed to an immunoconjugate comprising: a nanoparticle; a therapeutic radioisotope (e.g., wherein the radioisotope is attached to the nanoparticle via a second chelator) (e.g., wherein the radioisotope is a therapeutic radioisotope); and an antibody fragment conjugated to the nanoparticle (e.g., covalently or non-covalently bonded to the nanoparticle via a linker or covalently or non-covalently bonded directly to the nanoparticle, or associated with the nanoparticle or a composition surrounding the nanoparticle, e.g., via van der Waals forces), wherein the nanoparticle has a diameter (e.g., average diameter) no greater than 20 nanometers (e.g., as measured by dynamic light scattering (DLS) in aqueous solution, e.g., saline solution) (e.g., wherein the average nanoparticle diameter is from 1 to 20 nm, e.g., from 1 to 15 nm, e.g., from 1 to 10 nm, e.g., from 1 to 8 nm, e.g., from 4 to 10 nm, e.g., from 4 to 8 nm) (e.g., wherein the immunoconjugate has an average diameter no greater than 50 nm, e.g., no greater than 40 nm, e.g., no greater than 30 nm, e.g., no greater than 20 nm, e.g., no greater than 15 nm, e.g., no greater than 10 nm) (e.g., wherein the nanoparticle is coated with an organic polymer (e.g., polyethylene glycol (PEG)) (e.g., wherein immunoconjugate comprises a chelator) for use in a method of treating a disease or condition in a subject, wherein the treating comprises: delivering the immunoconjugate to the subject.

In another aspect, the invention is directed to an immunoconjugate comprising a nanoparticle; and an antibody fragment conjugated to the nanoparticle (e.g., covalently or non-covalently bonded to the nanoparticle via a linker or covalently or non-covalently bonded directly to the nanoparticle, or associated with the nanoparticle or a composition surrounding the nanoparticle, e.g., via van der Waals forces), wherein the nanoparticle has a diameter (e.g., average diameter) no greater than 20 nanometers (e.g., as measured by dynamic light scattering (DLS) in aqueous solution, e.g., saline solution) (e.g., wherein the average nanoparticle diameter is from 1 to 20 nm, e.g., from 1 to 15 nm, e.g., from 1 to 10 nm, e.g., from 1 to 8 nm, e.g., from 4 to 10 nm, e.g., from 4 to 8 nm) (e.g., wherein the immunoconjugate has an average diameter no greater than 50 nm, e.g., no greater than 40 nm, e.g., no greater than 30 nm, e.g., no greater than 20 nm, e.g., no greater than 15 nm, e.g., no greater than 10 nm) (e.g., wherein the nanoparticle is coated with an organic polymer (e.g., polyethylene glycol (PEG)) (e.g., wherein immunoconjugate comprises a chelator), and wherein the immunoconjugate comprises an imaging agent, for use in a method of in vivo diagnosis of a disease or condition in a subject, wherein the in vivo diagnosis comprises: delivering the immunoconjugate to the subject; and detecting (e.g., via PET, X-ray, MRI, CT, etc.) the imaging agent.

In another aspect, the invention is directed to an immunoconjugate comprising: a nanoparticle; and an antibody fragment conjugated to the nanoparticle (e.g., covalently or non-covalently bonded to the nanoparticle via a linker or covalently or non-covalently bonded directly to the nanoparticle, or associated with the nanoparticle or a composition surrounding the nanoparticle, e.g., via van der Waals forces), wherein the nanoparticle has a diameter (e.g., average diameter) no greater than 20 nanometers (e.g., as measured by dynamic light scattering (DLS) in aqueous solution, e.g., saline solution) (e.g., wherein the average nanoparticle diameter is from 1 to 20 nm, e.g., from 1 to 15 nm, e.g., from 1 to 10 nm, e.g., from 1 to 8 nm, e.g., from 4 to 10 nm, e.g., from 4 to 8 nm) (e.g., wherein the immunoconjugate has an average diameter no greater than 50 nm, e.g., no greater than 40 nm, e.g., no greater than 30 nm, e.g., no greater than 20 nm, e.g., no greater than 15 nm, e.g., no greater than 10 nm) (e.g., wherein the nanoparticle is coated with an organic polymer (e.g., polyethylene glycol (PEG)) (e.g., wherein immunoconjugate comprises a chelator), and wherein the immunoconjugate comprises an imaging agent, for use in (a) a method of treating a disease or condition in a subject or (b) a method of in vivo diagnosis of a disease or condition in a subject, wherein the method comprises: administering to a subject a pharmaceutical composition comprising the immunoconjugate (e.g., to target a particular type of tissue, e.g., cancer); and optionally, detecting (e.g., via PET, X-ray, MRI, CT, etc.) the imaging agent.

In another aspect, the invention is directed to an immunoconjugate comprising a nanoparticle; and an antibody fragment conjugated to the nanoparticle (e.g., covalently or non-covalently bonded to the nanoparticle via a linker or covalently or non-covalently bonded directly to the nanoparticle, or associated with the nanoparticle or a composition surrounding the nanoparticle, e.g., via van der Waals forces), wherein the nanoparticle has a diameter (e.g., average diameter) no greater than 20 nanometers (e.g., as measured by dynamic light scattering (DLS) in aqueous solution, e.g., saline solution) (e.g., wherein the average nanoparticle diameter is from 1 to 20 nm, e.g., from 1 to 15 nm, e.g., from 1 to 10 nm, e.g., from 1 to 8 nm, e.g., from 4 to 10 nm, e.g., from 4 to 8 nm) (e.g., wherein the immunoconjugate has an average diameter no greater than 50 nm, e.g., no greater than 40 nm, e.g., no greater than 30 nm, e.g., no greater than 20 nm, e.g., no greater than 15 nm, e.g., no greater than 10 nm) (e.g., wherein the nanoparticle is coated with an organic polymer (e.g., polyethylene glycol (PEG)) (e.g., wherein immunoconjugate comprises a chelator) for use in therapy.

In another aspect, the invention is directed to an immunoconjugate comprising: a nanoparticle; a therapeutic radioisotope (e.g., wherein the radioisotope is attached to the nanoparticle via a second chelator) (e.g., wherein the radioisotope is a therapeutic radioisotope); and an antibody fragment conjugated to the nanoparticle (e.g., covalently or non-covalently bonded to the nanoparticle via a linker or covalently or non-covalently bonded directly to the nanoparticle, or associated with the nanoparticle or a composition surrounding the nanoparticle, e.g., via van der Waals forces), wherein the nanoparticle has a diameter (e.g., average diameter) no greater than 20 nanometers (e.g., as measured by dynamic light scattering (DLS) in aqueous solution, e.g., saline solution) (e.g., wherein the average nanoparticle diameter is from 1 to 20 nm, e.g., from 1 to 15 nm, e.g., from 1 to 10 nm, e.g., from 1 to 8 nm, e.g., from 4 to 10 nm, e.g., from 4 to 8 nm) (e.g., wherein the immunoconjugate has an average diameter no greater than 50 nm, e.g., no greater than 40 nm, e.g., no greater than 30 nm, e.g., no greater than 20 nm, e.g., no greater than 15 nm, e.g., no greater than 10 nm) (e.g., wherein the nanoparticle is coated with an organic polymer (e.g., polyethylene glycol (PEG)) (e.g., wherein immunoconjugate comprises a chelator) for use in therapy.

In another aspect, the invention is directed to an immunoconjugate comprising: a nanoparticle; and an antibody fragment conjugated to the nanoparticle (e.g., covalently or non-covalently bonded to the nanoparticle via a linker or covalently or non-covalently bonded directly to the nanoparticle, or associated with the nanoparticle or a composition surrounding the nanoparticle, e.g., via van der Waals forces), wherein the nanoparticle has a diameter (e.g., average diameter) no greater than 20 nanometers (e.g., as measured by dynamic light scattering (DLS) in aqueous solution, e.g., saline solution) (e.g., wherein the average nanoparticle diameter is from 1 to 20 nm, e.g., from 1 to 15 nm, e.g., from 1 to 10 nm, e.g., from 1 to 8 nm, e.g., from 4 to 10 nm, e.g., from 4 to 8 nm) (e.g., wherein the immunoconjugate has an average diameter no greater than 50 nm, e.g., no greater than 40 nm, e.g., no greater than 30 nm, e.g., no greater than 20 nm, e.g., no greater than 15 nm, e.g., no greater than 10 nm) (e.g., wherein the nanoparticle is coated with an organic polymer (e.g., polyethylene glycol (PEG)) (e.g., wherein immunoconjugate comprises a chelator), and wherein the immunoconjugate comprises an imaging agent, for use in in vivo diagnosis.

In another aspect, the invention is directed to a composition (e.g., pharmaceutical composition) comprising: a nanoparticle; and a therapeutic radioisotope conjugated to the nanoparticle (e.g., covalently or non-covalently bonded to the nanoparticle via a linker or covalently or non-covalently bonded directly to the nanoparticle, or associated with the nanoparticle or a composition surrounding the nanoparticle, e.g., via van der Waals forces), wherein the nanoparticle has a diameter (e.g., average diameter) no greater than 20 nanometers (e.g., as measured by dynamic light scattering (DLS) in aqueous solution, e.g., saline solution) (e.g., wherein the average nanoparticle diameter is from 1 to 20 nm, e.g., from 1 to 15 nm, e.g., from 1 to 10 nm, e.g., from 1 to 8 nm, e.g., from 4 to 10 nm, e.g., from 4 to 8 nm) (e.g., wherein the nanoparticle is coated with an organic polymer (e.g., polyethylene glycol (PEG)) (e.g., wherein immunoconjugate comprises a chelator)) for use in a method of treating a disease or condition in a subject, wherein the treating comprises: delivering the composition to the subject; and delivering immunotherapy (e.g., wherein the immunotherapy comprises administering to a subject a pharmaceutical composition comprising the immunoconjugate).

Elements of embodiments involving one aspect of the invention (e.g., methods) can be applied in embodiments involving other aspects of the invention (e.g., systems), and vice versa.

DEFINITIONS

In order for the present disclosure to be more readily understood, certain terms are first defined below. Additional definitions for the following terms and other terms are set forth throughout the specification.

In this application, the use of "or" means "and/or" unless stated otherwise. As used in this application, the term "comprise" and variations of the term, such as "comprising" and "comprises," are not intended to exclude other additives, components, integers or steps. As used in this application, the terms "about" and "approximately" are used as equivalents. Any numerals used in this application with or without about/approximately are meant to cover any normal fluctuations appreciated by one of ordinary skill in the relevant art. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

"Administration": The term "administration" refers to introducing a substance into a subject. In general, any route of administration may be utilized including, for example, parenteral (e.g., intravenous), oral, topical, subcutaneous, peritoneal, intraarterial, inhalation, vaginal, rectal, nasal, introduction into the cerebrospinal fluid, or instillation into body compartments. In certain embodiments, administration is oral. Additionally or alternatively, in certain embodiments, administration is parenteral. In certain embodiments, administration is intravenous.

"Antibody": As used herein, the term "antibody" refers to a polypeptide that includes canonical immunoglobulin sequence elements sufficient to confer specific binding to a particular target antigen. Intact antibodies as produced in nature are approximately 150 kD tetrameric agents comprised of two identical heavy chain polypeptides (about 50 kD each) and two identical light chain polypeptides (about 25 kD each) that associate with each other into what is commonly referred to as a "Y-shaped" structure. Each heavy chain is comprised of at least four domains (each about 110 amino acids long)—an amino-terminal variable (VH) domain (located at the tips of the Y structure), followed by three constant domains: $CH_1$, $CH_2$, and the carboxy-terminal $CH_3$ (located at the base of the Y's stem). A short region, known as the "switch", connects the heavy chain variable and constant regions. The "hinge" connects $CH_2$ and $CH_3$ domains to the rest of the antibody. Two disulfide bonds in this hinge region connect the two heavy chain polypeptides to one another in an intact antibody. Each light chain is comprised of two domains—an amino-terminal variable (VL) domain, followed by a carboxy-terminal constant (CL) domain, separated from one another by another "switch". Intact antibody tetramers are comprised of two heavy chain-light chain dimers in which the heavy and light chains are linked to one another by a single disulfide bond; two other disulfide bonds connect the heavy chain hinge regions to one another, so that the dimers are connected to one another and the tetramer is formed. Naturally-produced antibodies are also glycosylated, typically on the $CH_2$ domain. Each domain in a natural antibody has a structure characterized by an "immunoglobulin fold" formed from two beta sheets (e.g., 3-, 4-, or 5-stranded sheets) packed against each other in a compressed antiparallel beta barrel. Each variable domain contains three hypervariable loops known as "complement determining regions" (CDR1, CDR2, and CDR3) and four somewhat invariant "framework" regions (FR1, FR2, FR3, and FR4). When natural antibodies fold, the FR regions form the beta sheets that provide the structural framework for the domains, and the CDR loop regions from both the heavy and light chains are brought together in three-dimensional space so that they create a single hypervariable antigen binding site located at the tip of the Y structure. The Fc region of naturally-occurring antibodies binds to elements of the complement system, and also to receptors on effector cells, including for example effector cells that mediate cytotoxicity. Affinity and/or other binding attributes of Fc regions for Fc receptors can be modulated through glycosylation or other modification. In certain embodiments, antibodies produced and/or utilized in accordance with the present invention include glycosylated Fc domains, including Fc domains with modified or engineered such glycosylation. For purposes of the present invention, in certain embodiments, any polypeptide or complex of polypeptides that includes sufficient immunoglobulin domain sequences as found in natural antibodies can be referred to and/or used as an "antibody", whether such polypeptide is naturally produced (e.g., generated by an organism reacting to an antigen), or produced by recombinant engineering, chemical synthesis, or other artificial system or methodology. In certain embodiments, an antibody is polyclonal; in certain embodiments, an antibody is monoclonal. In certain embodiments, an antibody has constant region sequences that are characteristic of mouse, rabbit, primate, or human antibodies. In certain embodiments, antibody sequence elements are humanized, primatized, chimeric, etc, as is known in the art. Moreover, the term "antibody" as used herein, can refer in appropriate embodiments (unless otherwise stated or clear from context) to any of the art-known or developed constructs or formats for utilizing antibody structural and functional features in alternative presentation. For example, embodiments, an antibody utilized in accordance with the present invention is in a format selected from, but not limited to, intact IgG, IgE and IgM, bi- or multi-specific antibodies (e.g., Zybodies®, etc), single chain Fvs, polypeptide-Fc fusions, Fabs, cameloid antibodies, masked antibodies (e.g., Probodies®), Small Modular ImmunoPharmaceuticals ("SMIPs™"), single chain or Tandem diabodies (TandAb®), VHHs, Anticalins®, Nanobodies®, minibodies, BiTE®s, ankyrin repeat proteins or DARPINs®, Avimers®, a DART, a TCR-like antibody, Adnectins®, Affilins®, Trans-Bodies®, Affibodies®, a TrimerX®, MicroProteins, Fynomers®, Centyrins®, and a KALBITOR®. In certain embodiments, an antibody may lack a covalent modification (e.g., attachment of a glycan) that it would have if produced naturally. In certain embodiments, an antibody may contain a covalent modification (e.g., attachment of a glycan, a payload [e.g., a detectable moiety, a therapeutic moiety, a catalytic moiety, etc], or other pendant group [e.g., poly-ethylene glycol, etc.]).

"Antibody fragment": As used herein, an "antibody fragment" includes a portion of an intact antibody, such as, for example, the antigen-binding or variable region of an antibody. Examples of antibody fragments include Fab, Fab', F(ab')2, and Fv fragments; triabodies; tetrabodies; linear antibodies; single-chain antibody molecules; and multi specific antibodies formed from antibody fragments. For example, antibody fragments include isolated fragments, "Fv" fragments, consisting of the variable regions of the heavy and light chains, recombinant single chain polypeptide molecules in which light and heavy chain variable regions are connected by a peptide linker ("ScFv proteins"), and minimal recognition units consisting of the amino acid residues that mimic the hypervariable region. In many embodiments, an antibody fragment contains sufficient sequence of the parent antibody of which it is a fragment that it binds to the same antigen as does the parent antibody; in certain embodiments, a fragment binds to the antigen with a comparable affinity to that of the parent antibody and/or competes with the parent antibody for binding to the antigen. Examples of antigen binding fragments of an antibody include, but are not limited to, Fab fragment, Fab' fragment, F(ab')2 fragment, scFv fragment, Fv fragment, dsFv diabody, dAb fragment, Fd' fragment, Fd fragment, and an isolated complementarity determining region (CDR) region. An antigen binding fragment of an antibody may be produced by any means. For example, an antigen binding fragment of an antibody may be enzymatically or chemically produced by fragmentation of an intact antibody and/or it may be recombinantly produced from a gene encoding the partial antibody sequence. Alternatively or additionally, antigen binding fragment of an antibody may be wholly or partially synthetically produced. An antigen binding fragment of an antibody may optionally comprise a single chain antibody fragment. Alternatively or additionally, an antigen binding fragment of an antibody may comprise multiple chains which are linked together, for example, by disulfide linkages. An antigen binding fragment of an antibody may optionally comprise a multimolecular complex. A functional single domain antibody fragment is in a range from about 5 kDa to about 25 kDa, e.g., from about 10 kDa to about 20 kDa, e.g., about 15 kDa; a functional single-chain fragment is from about 10 kDa to about 50 kDa, e.g., from about 20 kDa to about 45 kDa, e.g., from about 25 kDa to about 30 kDa; and a functional fab fragment is from about 40 kDa to about 80 kDa, e.g., from about 50 kDa to about 70 kDa, e.g., about 60 kDa.

"Associated": As used herein, the term "associated" typically refers to two or more entities in physical proximity with one another, either directly or indirectly (e.g., via one or more additional entities that serve as a linking agent), to form a structure that is sufficiently stable so that the entities remain in physical proximity under relevant conditions, e.g., physiological conditions. In certain embodiments, associated moieties are covalently linked to one another. In certain embodiments, associated entities are non-covalently linked. In certain embodiments, associated entities are linked to one another by specific non-covalent interactions (e.g., by interactions between interacting ligands that discriminate between their interaction partner and other entities present in the context of use, such as, for example. streptavidin/avidin interactions, antibody/antigen interactions, etc.). Alternatively or additionally, a sufficient number of weaker non-covalent interactions can provide sufficient stability for moieties to remain associated. Exemplary non-covalent interactions include, but are not limited to, electrostatic interactions, hydrogen bonding, affinity, metal coordination, physical adsorption, host-guest interactions, hydrophobic interactions, pi stacking interactions, van der Waals interactions, magnetic interactions, electrostatic interactions, dipole-dipole interactions, etc.

"Biocompatible": The term "biocompatible", as used herein is intended to describe materials that do not elicit a substantial detrimental response in vivo. In certain embodiments, the materials are "biocompatible" if they are not toxic to cells. In certain embodiments, materials are "biocompatible" if their addition to cells in vitro results in less than or equal to 20% cell death, and/or their administration in vivo does not induce inflammation or other such adverse effects. In certain embodiments, materials are biodegradable.

"Biodegradable": As used herein, "biodegradable" materials are those that, when introduced into cells, are broken down by cellular machinery (e.g., enzymatic degradation) or by hydrolysis into components that cells can either reuse or dispose of without significant toxic effects on the cells. In certain embodiments, components generated by breakdown of a biodegradable material do not induce inflammation and/or other adverse effects in vivo. In certain embodiments, biodegradable materials are enzymatically broken down. Alternatively or additionally, in certain embodiments, biodegradable materials are broken down by hydrolysis. In certain embodiments, biodegradable polymeric materials break down into their component polymers. In certain embodiments, breakdown of biodegradable materials (including, for example, biodegradable polymeric materials) includes hydrolysis of ester bonds. In certain embodiments, breakdown of materials (including, for example, biodegradable polymeric materials) includes cleavage of urethane linkages.

"Carrier": As used herein, "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin.

"Imaging agent": As used herein, "imaging agent" refers to any element, molecule, functional group, compound, fragments thereof or moiety that facilitates detection of an agent (e.g., a polysaccharide nanoparticle) to which it is joined. Examples of imaging agents include, but are not limited to: various ligands, radionuclides (e.g., $^{3}H$, $^{14}C$, $^{18}F$, $^{19}F$, $^{32}P$, $^{35}S$, $^{135}I$, $^{125}I$, $^{123}I$, $^{131}I$, $^{64}Cu$, $^{68}Ga$, $^{187}Re$, $^{111}In$, $^{90}Y$, $^{99m}Tc$, $^{177}Lu$, $^{89}Zr$ etc.), fluorescent dyes (for specific exemplary fluorescent dyes, see below), chemiluminescent agents (such as, for example, acridinum esters, stabilized dioxetanes, and the like), bioluminescent agents, spectrally resolvable inorganic fluorescent semiconductors nanocrystals (i.e., quantum dots), metal nanoparticles (e.g., gold, silver, copper, platinum, etc.) nanoclusters, paramagnetic metal ions, enzymes (for specific examples of enzymes, see below), colorimetric labels (such as, for example, dyes, colloidal gold, and the like), biotin, dioxigenin, haptens, and proteins for which antisera or monoclonal antibodies are available. The radionuclides may be attached via click chemistry, for example.

"Protein": As used herein, the term "protein" refers to a polypeptide (i.e., a string of at least 3-5 amino acids linked to one another by peptide bonds). Proteins may include moieties other than amino acids (e.g., may be glycoproteins, proteoglycans, etc.) and/or may be otherwise processed or modified. In certain embodiments "protein" can be a complete polypeptide as produced by and/or active in a cell (with or without a signal sequence); in certain embodiments, a "protein" is or comprises a characteristic portion such as a polypeptide as produced by and/or active in a cell. In certain embodiments, a protein includes more than one polypeptide chain. For example, polypeptide chains may be linked by one or more disulfide bonds or associated by other means. In certain embodiments, proteins or polypeptides as described herein may contain L-amino acids, D-amino acids, or both, and/or may contain any of a variety of amino acid modifications or analogs known in the art. Useful modifications include, e.g., terminal acetylation, amidation, methylation, etc. In certain embodiments, proteins or polypeptides may comprise natural amino acids, non-natural amino acids, synthetic amino acids, and/or combinations thereof. In certain embodiments, proteins are or comprise antibodies, antibody polypeptides, antibody fragments, biologically active portions thereof, and/or characteristic portions thereof.

"Pharmaceutical composition": As used herein, the term "pharmaceutical composition" refers to an active agent, formulated together with one or more pharmaceutically acceptable carriers. In certain embodiments, active agent is present in unit dose amount appropriate for administration in a therapeutic regimen that shows a statistically significant probability of achieving a predetermined therapeutic effect when administered to a relevant population. In certain embodiments, pharmaceutical compositions may be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin, lungs, or oral cavity; intravaginally or intrarectally, for example, as a pessary, cream, or foam; sublingually; ocularly; transdermally; or nasally, pulmonary, and to other mucosal surfaces.

"Substantially": As used herein, the term "substantially", and grammatic equivalents, refer to the qualitative condition of exhibiting total or near-total extent or degree of a characteristic or property of interest. One of ordinary skill in the art will understand that biological and chemical phenomena rarely, if ever, go to completion and/or proceed to completeness or achieve or avoid an absolute result.

"Subject": As used herein, the term "subject" includes humans and mammals (e.g., mice, rats, pigs, cats, dogs, and horses). In many embodiments, subjects are be mammals, particularly primates, especially humans. In certain embodiments, subjects are livestock such as cattle, sheep, goats, cows, swine, and the like; poultry such as chickens, ducks, geese, turkeys, and the like; and domesticated animals particularly pets such as dogs and cats. In certain embodiments (e.g., particularly in research contexts) subject mammals will be, for example, rodents (e.g., mice, rats, hamsters), rabbits, primates, or swine such as inbred pigs and the like.

"Therapeutic agent": As used herein, the phrase "therapeutic agent" refers to any agent that has a therapeutic effect and/or elicits a desired biological and/or pharmacological effect, when administered to a subject.

"Therapeutically effective amount": as used herein, is meant an amount that produces the desired effect for which it is administered. In certain embodiments, the term refers to an amount that is sufficient, when administered to a population suffering from or susceptible to a disease, disorder, and/or condition in accordance with a therapeutic dosing regimen, to treat the disease, disorder, and/or condition. In certain embodiments, a therapeutically effective amount is one that reduces the incidence and/or severity of, and/or delays onset of, one or more symptoms of the disease, disorder, and/or condition. Those of ordinary skill in the art will appreciate that the term "therapeutically effective amount" does not in fact require successful treatment be achieved in a particular individual. Rather, a therapeutically effective amount may be that amount that provides a particular desired pharmacological response in a significant number of subjects when administered to patients in need of such treatment. In certain embodiments, reference to a therapeutically effective amount may be a reference to an amount as measured in one or more specific tissues (e.g., a tissue affected by the disease, disorder or condition) or fluids (e.g., blood, saliva, serum, sweat, tears, urine, etc.). Those of ordinary skill in the art will appreciate that, in certain embodiments, a therapeutically effective amount of a particular agent or therapy may be formulated and/or administered in a single dose. In certain embodiments, a therapeutically effective agent may be formulated and/or administered in a plurality of doses, for example, as part of a dosing regimen.

"Treatment": As used herein, the term "treatment" (also "treat" or "treating") refers to any administration of a substance that partially or completely alleviates, ameliorates, relives, inhibits, delays onset of, reduces severity of, and/or reduces incidence of one or more symptoms, features, and/or causes of a particular disease, disorder, and/or condition. Such treatment may be of a subject who does not exhibit signs of the relevant disease, disorder and/or condition and/or of a subject who exhibits only early signs of the disease, disorder, and/or condition. Alternatively or additionally, such treatment may be of a subject who exhibits one or more established signs of the relevant disease, disorder and/or condition. In certain embodiments, treatment may be of a subject who has been diagnosed as suffering from the relevant disease, disorder, and/or condition. In certain embodiments, treatment may be of a subject known to have one or more susceptibility factors that are statistically correlated with increased risk of development of the relevant disease, disorder, and/or condition.

Drawings are presented herein for illustration purposes, not for limitation.

BRIEF DESCRIPTION OF DRAWINGS

The foregoing and other objects, aspects, features, and advantages of the present disclosure will become more apparent and better understood by referring to the following description taken in conduction with the accompanying drawings, in which:

FIG. 4A shows $^{89}$Zr labeling yields of C' dot-PEG-Mal under varied pH conditions at 75° C.

FIG. 4B shows $^{89}$Zr labeling yields of C' dot-PEG-Mal using varied combinations of C' dot to $^{89}$Zr-oxalate ratio.

FIGS. 5A and 5B show in vivo coronal PET images of [89Zr]C' dot-PEG at different post-injection time points (10 min, Day 1, Day 3 and Day 6) in a healthy nude mouse. [$^{89}$Zr]C' dot-PEG was synthesized by using a chelator-free radiolabeling technique. The PET images were acquired by using a Focus 120 MicroPET scanner.

FIG. 5A shows PET images acquired without EDTA (ethylenediaminetetraacetic acid).

FIG. 5B shows PET images acquired with EDTA

DETAILED DESCRIPTION

Figure 1:
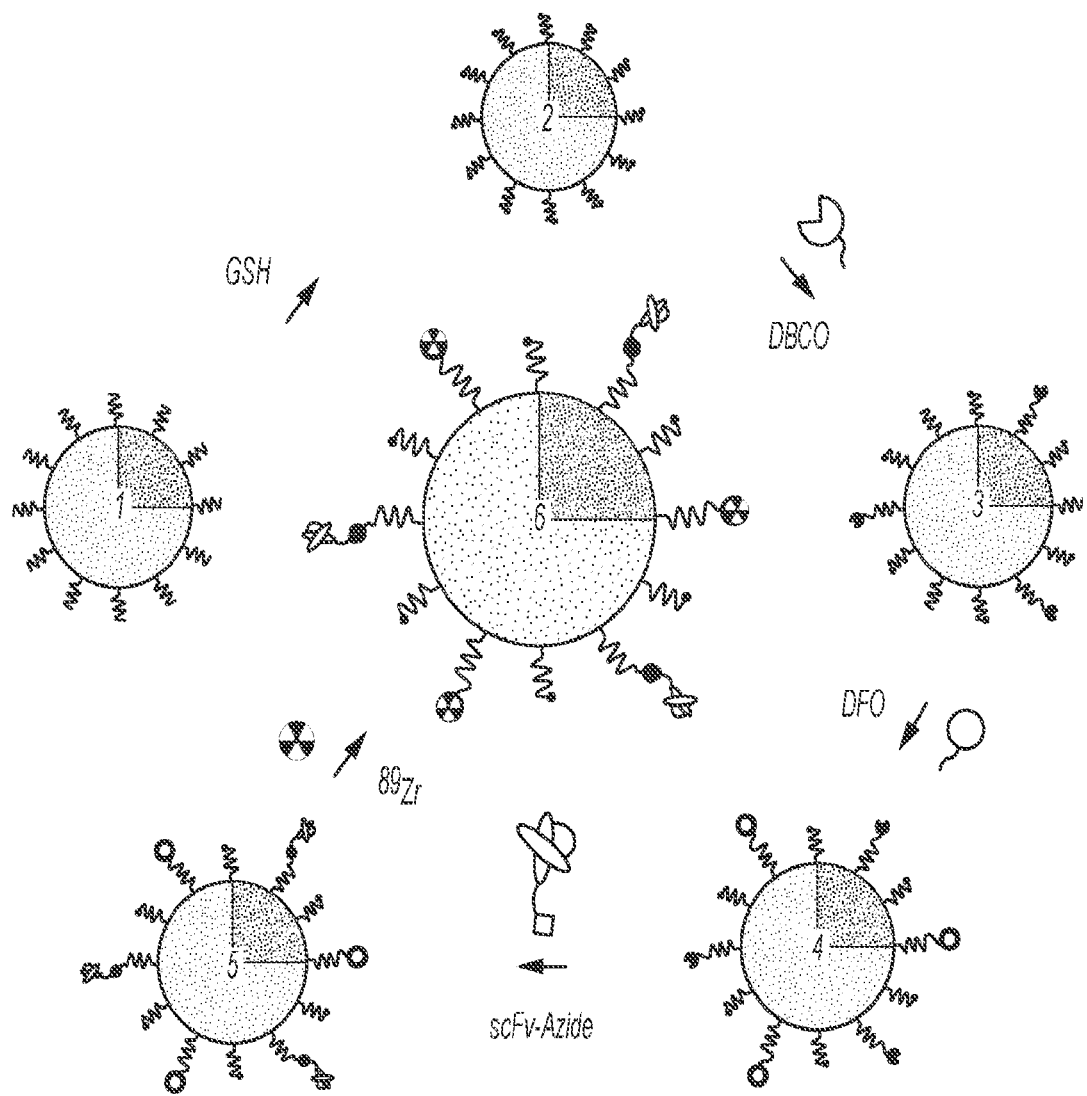
FIG. 1 shows a schematic illustration showing the synthesis of $^{89}$Zr-labeled C'dot radioimmunoconjugate using a chelator-based radiolabeling technique. PEGylated and maleimide-functionalized C' dot (C' dot-PEG-Mal, 1) was first reacted with reduced glutathione (GSH) to introduce the —NH$_2$ groups for the following-up bioconjugates, forming C' dot-PEG-GSH (2). Then the nanoparticle was conjugated with DBCO-PEG4-NHS ester and DFO-NCS, forming C' dot-PEG-DBCO (3) and DFO-C' dot-PEG-DBCO (4), respectively. Azide-functionalized small targeting ligands, such as single-chain variable fragment (scFv-azide) (or single-domain antibody, sdAb-azide), was conjugated to the nanoparticle based on strain-promoted azide-alkyne cycloaddition, forming DFO-C' dot-PEG-scFv (5). The final C'dot radioimmunoconjugate ($^{89}$Zr-DFO-C' dot-PEG-scFv, 6) was by labeling it with $^{89}$Zr-oxalate. The embodiments illustrated in FIG. 1 are not limited to scFv and can include various types of antibody fragments, e.g., sdAbs.

Throughout the description, where compositions are described as having, including, or comprising specific components, or where methods are described as having, including, or comprising specific steps, it is contemplated that, additionally, there are compositions of the present invention that consist essentially of, or consist of, the recited components, and that there are methods according to the present invention that consist essentially of, or consist of, the recited processing steps.

It should be understood that the order of steps or order for performing certain action is immaterial so long as the invention remains operable. Moreover, two or more steps or actions may be conducted simultaneously.

The mention herein of any publication, for example, in the Background section, is not an admission that the publication serves as prior art with respect to any of the claims presented herein. The Background section is presented for purposes of clarity and is not meant as a description of prior art with respect to any claim.

Molecular therapeutics (e.g., antibodies) can modulate the immune system toward antitumor activity by manipulating immune checkpoints (e.g., the monoclonal antibody ipilimumab inhibits CTLA4, a negative regulatory molecule that inhibits function of the immune system). The rationale is to trigger preexisting, but dormant, antitumor immune responses. Other molecules and pathways have acted as immune switches. PD-1, another negative regulatory receptor expressed on T cells, has also been targeted. Switching a single immune checkpoint may not be sufficient to induce an antitumor response, explaining some of the failures of targeting single immune regulatory checkpoints like PD-1 or CTLA4. However, without wishing to be bound to any theory, treatment can be bolstered by the addition of RT, which is thought, in some cases, to have immunomodulatory properties. In these cases, tumors outside of RT treatment fields have been found to shrink as a result of a putative systemic inflammatory or immune response provoked by RT, highlighting the potential for radiation to spark a systemic antitumor immune response. Augmenting immune activity may also potentiate the local effects of RT.

By raising the concentration alone of these immunoconjugates, disease can be treated. A therapeutic radiolabel can also be added to further treat disease. In certain embodiments, the immunoconjugate act as a therapeutic at high concentrations, and without a therapeutic radiolabel. In certain embodiments, the radiolabel is attached to the same nanoparticle in an all-in-one multi-therapeutic platform. Alternatively, therapeutic radioisotopes can be administered independently.

Described herein are target-specific nanoparticle immunoconjugates (e.g., single chain antibody fragments bound to the particle surface) for targeted diagnostic and/or therapeutic platforms. In certain embodiments, the nanoparticle immunoconjugates are less than 20 nm (e.g., 6 to 10 nm) in diameter. This small size is found to offer advantages in therapeutic and/or imaging applications. For example, the disclosed immunoconjugates may offer improved targeting of diseased tissue and reduced non-specific uptake by organs (e.g., by the liver). The smaller immunoconjugates may also demonstrate reduced immune reactivity, thereby further improving efficacy.

In certain embodiments, the nanoparticle comprises silica, polymer (e.g., poly(lactic-co-glycolic acid) (PLGA)), and/or metal (e.g., gold, iron).

In certain embodiments, the silica-based nanoparticle platform comprises ultrasmall nanoparticles or "C dots," which are fluorescent, organo-silica core shell particles that have diameters controllable down to the sub-10 nm range with a range of modular functionalities. C dots are described by U.S. Pat. No. 8,298,677 B2 "Fluorescent silica-based nanoparticles", U.S. Publication No. 2013/0039848 A1 "Fluorescent silica-based nanoparticles", and U.S. Publication No. US 2014/0248210 A1 "Multimodal silica-based nanoparticles", the contents of which are incorporated herein by reference in their entireties. Incorporated into the silica matrix of the core are near-infrared dye molecules, such as Cy5.5, which provides its distinct optical properties. Surrounding the core is a layer or shell of silica. The silica surface is covalently modified with silyl-polyethylene glycol (PEG) groups to enhance stability in aqueous and biologically relevant conditions. These particles have been evaluated in vivo and exhibit excellent clearance properties owing largely to their size and inert surface. Among the additional functionalities incorporated into C dots are chemical sensing, non-optical (PET) image contrast and in vitro/in vivo targeting capabilities, which enable their use in visualizing lymph nodes for surgical applications, and melanoma detection in cancer.

In certain embodiments, a chemotherapy drug is a chemotherapy drug as described in U.S. Publication No. US 2014/0248210 A1, which relates to nanoparticles. For example, therapeutic agents that may be attached to the present nanoparticle include, but are not limited to, DNA alkylating agents, topoisomerase inhibitors, endoplasmic reticulum stress inducing agents, a platinum compound, an antimetabolite, vincalkaloids, taxanes, epothilones, enzyme inhibitors, receptor antagonists, therapeutic antibodies, tyrosine kinase inhibitors, boron radiosensitizers (i.e. velcade), and chemotherapeutic combination therapies. Non-limiting examples of Topoisomerase I inhibitors include Campothecin derivatives including CPT-11 (irinotecan), SN-38, APC, NPC, campothecin, topotecan, exatecan mesylate, 9-nitro-camptothecin, 9-aminocamptothecin, lurtotecan rubitecan, silatecan, gimatecan, diflomotecan, extatecan, BN-80927, DX-8951f, and MAG-CPT as described in Pommier Y. (2006) *Nat. Rev. Cancer* 6(10):789-802 and U.S. Patent Publication No. 200510250854; Protoberberine alkaloids and derivatives thereof including berberrubine and coralyne as described in Li et al. (2000) *Biochemistry* 39(247107-7116 and Gatto et al. (1996) *Cancer Res.* 15(12):2795-2800; Phenanthroline derivatives including Benzo[i]phenanthridine, Nitidine, and fagaronine as described in Makhey et al.

(2003) *Bioorg. Med. Chem.* 11 (8): 1809-1820; Terbenzimidazole and derivatives thereof as described in Xu (1998) *Biochemistry* 37(10):3558-3566, and Anthracycline derivatives including Doxorubicin, Daunorubicin, and Mitoxantrone as described in Foglesong et al. (1992) *Cancer Chemother. Pharmacol.* 30(2):123-]25, Crow et al. (1994) *J. Med. Chem.* 37(19):31913194, and Crespi et al. (1986) *Biochem. Biophys. Res. Common.* 136(2):521-8. Topoisomerase II inhibitors include, but are not limited to Etoposide and Teniposide. Dual topoisomerase I and II inhibitors include, but are not limited to, Saintopin and other Naphthecenediones, DACA and other Acridine-4-Carboxamindes, Intoplicine and other Benzopyridoindoles, TAS-I03 and other 7H-indeno[2,1-c]Quinoline-7-ones, Pyrazoloacridine, XR 11576 and other Benzophenazines, XR 5944 and other Dimeric compounds, 7-oxo-7H-dibenz[f,ij]Isoquinolines and 7-oxo-7H-benzo[e]Perimidines, and Anthracenyl-amino Acid Conjugates as described in Denny and Baguley (2003) *Curr. Top. Med. Chem.* 3(3):339-353. Some agents inhibit Topoisomerase II and have DNA intercalation activity such as, but not limited to, Anthracyclines (Aclarubicin, Daunorubicin, Doxorubicin, Epirubicin, Idarubicin, Amrubicin, Pirarubicin, Valrubicin, Zorubicin) and Antracenediones (Mitoxantrone and Pixantrone).

C dots are synthesized via an alcohol-based modified Stöber process. C'dots are synthesized in water.

C dots or C'dots provide a unique platform for drug delivery due to their physical properties as well as demonstrated human in vivo characteristics. These particles are ultrasmall and benefit from EPR effects in tumor microenvironments, while retaining desired clearance and pharmacokinetic properties. To this end, described herein is a nanoparticle drug delivery system in which, in certain embodiments, drug constructs are covalently attached to C dots or C'dots (or other nanoparticles).

C dots or C'dots can serve as highly specific and potent multi-therapeutic targeted particle probes to combine antibody fragments with therapeutic radiolabels (e.g., $^{177}$Lu, $^{225}$Ac, $^{99}$Y, $^{89}$Zr) on a single platform. Alternatively, C dot or C'dot coupling of targeting peptides, such as alphaMSH, known to be immunomodulatory and anti-inflammatory in nature, can also be combined with C dot or C'dot radiotherapeutic (and/or other particle-based) platforms to achieve enhanced efficacy. In certain embodiments, the concentration of the radioisotope and/or antibody fragment is higher in therapeutic applications compared to diagnostic applications.

In contrast to other multimodal platforms, immunoconjugates can comprise different moieties that are attached to the nanoparticle itself. For example, in certain embodiments, a radioisotope is attached to the nanoparticle and an antibody fragment is attached to the nanoparticle—that is, in these embodiments, the radiolabel is not attached to the antibody fragment itself. As another example, immunoconjugates can comprise a targeting ligand attached to the nanoparticle, a radioisotope attached to the nanoparticle, and an antibody fragment attached to the nanoparticle. The stoichiometric ratios of different moieties attached to the C dot will affect the biodistribution of the nanoparticle immunoconjugate.

Figure 8:
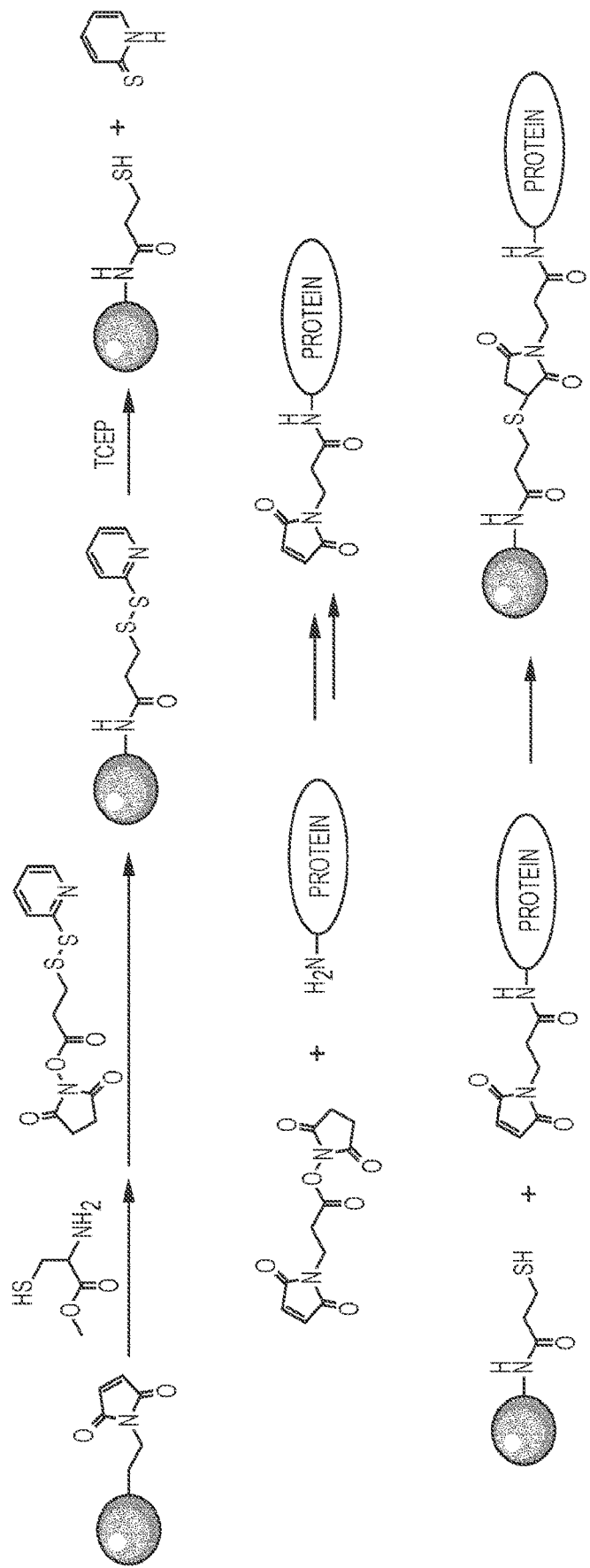
FIG. 8 shows an exemplary schematic of thiol-maleimide chemistry.

The immunoconjugates, e.g., C dot-antibody (mAb) and -antibody-fragment (vFab) conjugates, can be prepared using either of two approaches. Scheme 1 comprises thiol-maleimide chemistry, as shown in FIG. 8. Scheme 1 is designed around proteins modified to contain maleimide groups. Scheme 2 comprises alkene-tetrazine chemistry as shown in FIG. 9.

In Scheme 1 as shown in FIG. 8, C dots containing Cy5 dye, surface functionalized with PEG and maleimide groups (C dots-(Cy5)-PEG-mal) were prepared as previously described in Bradbury et al., 2014. Silanes modified with the Cy5 fluorophore were prepared and titrated with tetramethylorthosilane (TMOS) into a dilute solution of $NH_4OH$ (molar ratio TMOS:Cy5:NH3:H20 is 1:0.001:0.44:1215) and allowed to mix for 24 hours (Urata C, Aoyama Y, Tonegawa A, Yamauchi Y, Kuroda K. Dialysis process for the removal of surfactants to form colloidal mesoporous silica nanoparticles. Chem Commun (Camb). 2009; (34): 5094-6) (Yamada H, Urata C, Aoyama Y, Osada S, Yamauchi Y, Kuroda K. Preparation of Colloidal Mesoporous Silica Nanoparticles with Different Diameters and Their Unique Degradation Behavior in Static Aqueous Systems, Chem. Mater. 2012; 24(8):1462-71.) (Wang J, Sugawara-Narutaki A, Fukao M, Yokoi T, Shimojima A, Okubo T. Two-phase synthesis of monodisperse silica nanospheres with amines or ammonia catalyst and their controlled self-assembly. ACS Appl Mater Interfaces. 2011; 3(5):1538-44.) This resulted in a Cy5 encapsulated silica particle, the surface of which was further PEGylated and functionalized with maleimide groups by treatment with PEG-silane (500 g/mole) (Suzuki K, Ikari K, Imai H. Synthesis of silica nanoparticles having a well-ordered mesostructured using a double surfactant system. J Am Chem Soc. 2004; 126(2): 462-3) and maleimide-PEG-silane (molar ratio PEG-silane:TMOS:mal-PEG-silane of 1:2.3:0.006). The maleimide groups can then be effectively transformed into amine groups by reacting the particles with compounds that contain a thiol and amine (e.g., cysteine methyl ester or cysteamine-HCl). The resulting C dot-(Cy5)-PEG-amine can then be subsequently modified with a succinimidyl 3-(2-pyridyldithio)propionate (SPDP). The pyridyldithiol serves at least two purposes: one, it can be used to quantitate conjugation efficiencies; two, it may serves as a 'protecting group' to minimize oxidation of thiol groups; etc. TCEP can then be used to remove the group releasing a pyridine 2-thione, which can be measured by HPLC or UV-absorption for quantitation. The resulting C dot-(Cy5)-PEG-thiol can then be reacted with protein-maleimide leading to the desired C dot-(Cy5)-PEG-mAb or C dot-(Cy5)-PEG-vFab.

Figure 9:
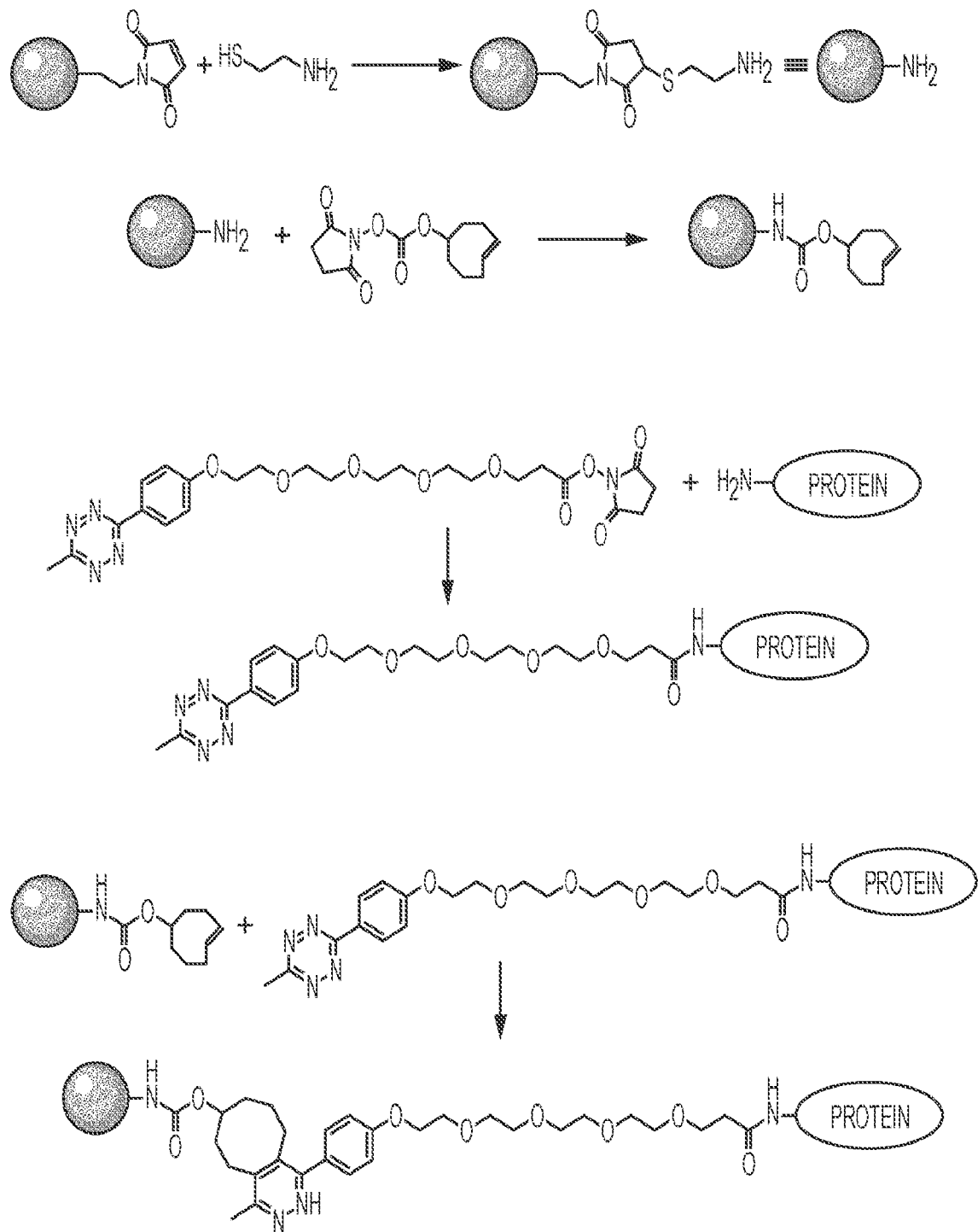
FIG. 9 shows an exemplary schematic of alkene-tetrazine chemistry.

In Scheme 2 as shown in FIG. 9, alkene-tetrazine chemistry is utilized for protein attachment. Here, the mAb or vFab is modified with a click reactive groups, such as methyltetrazine-$PEG_4$-NHS ester. The C dot-(Cy5)-PEG-amine, as described in FIG. 8 (Scheme 1), is then modified with the appropriate click partner, (e.g., TCO-PEG4-NHS ester). In the final step, the methyltetrazine-mAb or -vFab can then be reacted with the C dot-(Cy5)-PEG-TCO leading to the C dot-(Cy5)-PEG-mAb or C dot-(Cy5)-PEG-vFab product.

Antibody fragments (fAbs) provide advantages (e.g., size, no Fc region for reduced immunogenicity, scalability, and adaptability) compared to standard monoclonal antibodies (mAbs). fAbs are the stripped-down binding region of an antibody which is usually expressed as a single continuous sequence in an expression host (e.g., *E. Coli*). In certain embodiments, a fAb or mAb can be as small as 15 kDa (+/−5 kDa) (e.g., about 3 nm). In other embodiments, a fAb or mAb can be up to 150 kDa (e.g., up to 20 nm). In one embodiment, a fAb is approximately 60 kDa (e.g., +/−15 kDa). A fAb comprises an immunoglobin heavy-chain variable and constant domain linked to the corresponding domains of an immunoglobin light chain. In another embodiment, the antibody format can be a single chain variable fragment (scFv) fragment that is approximately 30 kDa (e.g., +/−10 kDa). A scFv fragment comprises a heavy-chain variable domain linked to a light-chain variable domain. In other embodiments, the antibody format can be a single domain antibody (sdAb) fragment that is approximately 15 kDa (e.g., +/−5 kDa). A sdAb fragment comprises a single heavy-chain variable domain. In certain embodiments, the antibody fragment is an anti-CEA scFv for targeting different tumors.

In certain embodiments, various linkers are used. In certain embodiments, a cleavable linker (e.g., peptide, hydrazine, or disulfide) is used. In certain embodiments, a noncleavable linker (e.g., thioether) is used. In certain embodiments, a peptide linker is selectively cleaved by lysosomal proteases (e.g., cathepsin-B). In certain embodiments, a valine-citrulline dipeptide linker is used.

In certain embodiments, a linker is a linker as described by U.S. Pat. No. 7,691,962, which relates to drug-ligand conjugates. In certain embodiments, the linkers are characterized by their ability to be cleaved at a site in or near the target cell such as at the site of therapeutic action or marker activity. Such cleavage can be enzymatic in nature. This feature aids in reducing systemic activation of the therapeutic agent or marker, reducing toxicity and systemic side effects. Preferred cleavable groups for enzymatic cleavage include peptide bonds, ester linkages, and disulfide linkages. In other embodiments, the linkers are sensitive to pH and are cleaved through changes in pH.

In certain embodiments, different linkers as described in U.S. Pat. Nos. 4,680,338, 5,122,368, 5,141,648, 5,208,020, 5,416,064, 5,475,092, 5,543,390, 5,563,250 5,585,499, 5,880,270, 6,214,345, 6,436,931, 6,372,738, 6,340,701, 6,989,452, 7,129,261, 7,375,078, 7,498,302, 7,507,420, 7,691,962, 7,910,594, 7,968,586, 7,989,434, 7,994,135, 7,999,083, 8,153,768, 8,236,319, Zhao, R.; et al, (2011) J. Med. Chem. 36, 5404; Doronina, S.; et al, (2006) Bioconjug Chem, 17, 114; Hamann, P.; et al. (2005) Bioconjug Chem. 16, 346, the contents of which are hereby incorporated by reference herein, are used.

In certain embodiments, the mAbs and/or fAbs are U.S. approved for certain uses. Non-limiting examples of mAbs and fAbs include anti-GPIIb/IIIa, anti-VEGF-A, and anti-TNF-α. ReoPro (abciximab) is an anti-GPIIb/IIIa, chimeric fAb, IgG1-κ developed by Centocor/Eli Lilly as described by Nelson and Reichert, "Development trends for therapeutic antibody fragments," Nature Biotechnology, 27(4), 2009. Lucentis (ranibizumab) is an anti-VEGF-A, humanized Fab IgG1-κ developed by Genentech (Nelson and Reichert, 2009) that is used to prevent wet age-related macular degeneration. Cimzia (certolizumab pegol), is an Anti-TNF-α, PEGylated humanized fAb developed by UCB (Nelson and Reichert, 2009) that is used to prevent moderate to severe Crohn's disease.

In certain embodiments, PET (Positron Emission Tomography) tracers are used as imaging agents. In certain embodiments, PET tracers comprise $^{89}$Zr, $^{64}$Cu, [$^{18}$F] fluorodeoxyglucose.

In certain embodiments, fluorophores comprise fluorochromes, fluorochrome quencher molecules, any organic or inorganic dyes, metal chelates, or any fluorescent enzyme substrates, including protease activatable enzyme substrates. In certain embodiments, fluorophores comprise long chain carbophilic cyanines. In other embodiments, fluorophores comprise DiI, DiR, DiD, and the like. Fluorochromes comprise far red, and near infrared fluorochromes (NIRF). Fluorochromes include but are not limited to a carbocyanine and indocyanine fluorochromes. In certain embodiments, imaging agents comprise commercially available fluorochromes including, but not limited to Cy5.5, Cy5 and Cy7 (GE Healthcare); AlexaFlour660, AlexaFlour680, AlexaFluor750, and AlexaFluor790 (Invitrogen); VivoTag680, VivoTag-S680, and VivoTag-S750 (VisEn Medical); Dy677, Dy682, Dy752 and Dy780 (Dyomics); DyLight547, DyLight647 (Pierce); HiLyte Fluor 647, HiLyte Fluor 680, and HiLyte Fluor 750 (AnaSpec); IRDye 800CW, IRDye 800RS, and IRDye 700DX (Li-Cor); and ADS780WS, ADS830WS, and ADS832WS (American Dye Source) and Kodak X-SIGHT 650, Kodak X-SIGHT 691, Kodak X-SIGHT 751 (Carestream Health).

In certain embodiments, click reactive groups are used (for 'click chemistry'). Examples of click reactive groups include the following: alkyne, azide, thiol (sulfydryl), alkene, acrylate, oxime, maliemide, NHS (N-hydroxysuccinimide), amine (primary amine, secondary amine, tertiary amine, and/or quarternary ammonium), phenyl, benzyl, hydroxyl, carbonyl, aldehyde, carbonate, carboxylate, carboxyl, ester, methoxy, hydroperoxy, peroxy, ether, hemiacetal, hemiketal, acetal, ketal, orthoester, orthocarbonate ester, amide, carboxyamide, imine (primary ketimine, secondary ketamine, primary aldimine, secondary aldimine), imide, azo (diimide), cyanate (cyanate or isocyanate), nitrate, nitrile, isonitrile, nitrite (nitrosooxy group), nitro, nitroso, pyridyl, sulfide, disulfide, sulfinyl, sulfonyl, sulfino, sulfo, thiocyanate, isothiocyanate, caronothioyl, thione, thial, phosphine, phosphono, phosphate, phosphodiester, borono, boronate, bornino, borinate, halo, fluoro, chloro, bromo, and/or iodo moieties.

Cancers that may be treated include, for example, prostate cancer, breast cancer, testicular cancer, cervical cancer, lung cancer, colon cancer, bone cancer, glioma, glioblastoma, multiple myeloma, sarcoma, small cell carcinoma, melanoma, renal cancer, liver cancer, head and neck cancer, esophageal cancer, thyroid cancer, lymphoma, and/or leukemia.

In certain embodiments, targeting peptide ligands, such as alpha-MSH, attached to C dots, can serve as immunomodulators alongside other therapies to enhance treatment response.

In certain embodiments, in addition to administration of an immunoconjugate described herein, a method of treatment may include administration of antibodies, small molecule drugs, radiation, pharmacotherapy, chemotherapy, cryotherapy, thermotherapy, electrotherapy, phototherapy, ultrasonic therapy and/or surgery.

In certain embodiments, the immunoconjugate comprises a therapeutic agent, e.g., a drug (e.g., a chemotherapy drug) and/or a therapeutic radioisotope. As used herein, "therapeutic agent" refers to any agent that has a therapeutic effect and/or elicits a desired biological and/or pharmacological effect, when administered to a subject.

In certain embodiments, the radioisotope is a radiolabel that can be monitored/imaged (e.g., via PET or single-photon emission computed tomography (SPECT)). Example radioisotopes that can be used include beta emitters (e.g. $^{177}$Luteium) and alpha emitters (e.g., $^{225}$Ac). In certain embodiments, one or more of the following radioisotopes are used: $^{99m}$Tc, $^{111}$In, $^{64}$Cu, $^{67}$Ga, $^{186}$Re, $^{188}$Re, $^{153}$Sm, $^{177}$Lu, $^{67}$Cu, $^{123}$I, $^{124}$I, $^{125}$I, $^{11}$C, $^{13}$N, $^{15}$O, $^{18}$F, $^{186}$Re, $^{188}$Re, $^{153}$Sm, $^{166}$Ho, $^{177}$Lu, $^{149}$Pm, $^{90}$Y, $^{213}$Bi, $^{103}$Pd, $^{109}$Pd, $^{159}$Gd, $^{140}$La, $^{198}$Au, $^{199}$Au, $^{169}$Yb, $^{175}$Yb, $^{165}$Dy, $^{166}$Dy, $^{67}$Cu, $^{105}$Rh, $^{111}$Ag, $^{89}$Zr, $^{225}$Ac, and $^{192}$Ir.

In certain embodiments, the immunoconjugate comprises one or more drugs, e.g., one or more chemotherapy drugs, such as sorafenib, paclitaxel, docetaxel, MEK162, etoposide, lapatinib, nilotinib, crizotinib, fulvestrant, vemurafenib, bexorotene, and/or camptotecin.

In certain embodiments, the immunoconjugate comprises a chelator, for example, 1,4,8,1 1-tetraazabicyclo[6.6.2]hexadecane-4,1 1-diyl)diacetic acid (CB-TE2A); desferoxamine (DFO); diethylenetriaminepentaacetic acid (DTPA); 1,4,7, 10-tetraazacyclotetradecane-1,4,7, 10-tetraacetic acid (DOTA); thylenediaminetetraacetic acid (EDTA); ethylene glycolbis(2-aminoethyl)-N,N,N',N'-tetraacetic acid (EGTA); 1,4,8,1 1-tetraazacyclotetradecane-1,4,8,1 1-tetraacetic acid (TETA); ethylenebis-(2-4 hydroxy-phenylglycine) (EHPG); 5-Cl-EHPG; 5Br-EHPG; 5-Me-EHPG; 5t-Bu-EHPG; 5-sec-Bu-EHPG; benzodiethylenetriamine pentaacetic acid (benzo-DTPA); dibenzo-DTPA; phenyl-DTPA, diphenyl-DTPA; benzyl-DTPA; dibenzyl DTPA; bis-2 (hydroxybenzyl)-ethylene-diaminediacetic acid (HBED) and derivatives thereof; Ac-DOTA; benzo-DOTA; dibenzo-DOTA; 1,4,7-triazacyclononane N,N',N"-triacetic acid (NOTA); benzo-NOTA; benzo-TETA, benzo-DOTMA, where DOTMA is 1,4,7, 10-tetraazacyclotetradecane-1,4,7, 10-tetra(methyl tetraacetic acid), benzo-TETMA, where TETMA is 1,4,8,1 1-tetraazacyclotetradecane-1,4,8,1 1-(methyl tetraacetic acid); derivatives of 1,3-propylenediaminetetraacetic acid (PDTA); triethylenetetraaminehexaacetic acid (TTHA); derivatives of 1,5,10-N,N',N"-tris (2,3-dihydroxybenzoyl)-tricatecholate (LICAM); and 1,3,5-N,N',N"-tris(2,3-dihydroxybenzoyl)aminomethylbenzene (MECAM), or other metal chelators.

In certain embodiments, the immunoconjugate comprises more than one chelator.

In certain embodiments the radioisotope-chelator pair is $^{89}$Zr-DFO. In certain embodiments the radioisotope-chelator pair $^{177}$Lu-DOTA. In certain embodiments, the is radioisotope-chelator pair is $^{225}$Ac-DOTA.

In certain embodiments, the therapeutic agent (e.g., drug and/or radioisotope) is attached to the nanoparticle or the antibody fragment (protein), or both, using a bioorthogonal conjugation approach (e.g., amine/NHS-ester, thiol/maleimide, azide/alkyne click, or tetrazine/TCO click). For radiolabeling using radiometals, the radiometal chelator can be first attached to either particle or protein or both, followed by the radiometal. Alternatively, the radiometal/chelator complex can be performed, followed by attachment onto the particle or protein or both. Radioiodination can also be achieved using standard approaches where a tyrosine or phenolic group on the particle or protein or both is modified by electrophilic addition chemistry.

In certain embodiments, the immunoconjugate is administered to a subject suffering from a particular disease or condition (e.g., cancer) for treatment of the disease or condition.

EXPERIMENTAL EXAMPLES

Preparation of the C Dot-(Cy5)-PEG-Maleimide:

A maleimide and NHS ester functionalized polyethylene glycol (mal-dPEG$_{12}$-NHS) was conjugated with aminosilane (APTES) in DMSO (molar ratio mal-PEG-NHS: APTES:DMSO 1:0.9:60). The reaction mixture was left under nitrogen at room temperature for 48 hours to generate silane functionalized mal-dPEG (mal-dPEG-APTES). A maleimide functionalized Cy5 (mal-Cy5) was reacted with a thiol-silane (MPTMS) in DMSO (molar ratio Cy5:MPTMS: DMOS 1:25:1150). The reaction was left under nitrogen at room temperature for 24 hours to generate a silane functionalized Cy5 (Cy5-MPTMS). TMOS and Cy5-MPTMS were then titrated into an ammonia hydroxide solution (~pH 8) (molar ratio TMOS:Cy5:NH3:H2O 1:0.001:0.44:1215). The solution was stirred at 600 rpm at room temperature for 24 hours to form homogeneous Cy5 encapsulated silica nanoparticles. The mal-dPEG-APTES and silane functionalized polyethylene glycol (PEG-silane, MW around 500, Gelest) were then added into the synthesis solution to PEGylate and surface-functionalize the particles (PEG-silane:TMOS:mal-PEG-APTES 1:2.3:0.006). The solution was stirred at 600 rpm at room temperature for 24 hours followed by incubation at 80° C. for another 24 hours without stirring. The solution was dialyzed in 2000 mL with deionized water for two days (10k MWCO), filtered with 200 nm syringe filters, and finally chromatographically purified (Superdex 200) resulting in the desired mal-C dots. Preparation of C Dot Immunoconjugates Studies were performed to conjugate single chain antibody fragments (scFv)s to the C dot core silica nanoparticles. An scFv that bound matrix metalloproteinase 12 (MMP-12) was expressed in *E. coli*. The construct contained C-terminal His and FLAG tags for nickel affinity chromatography and immune-detection. A mutant scFv was constructed in which the last amino acid of the polypeptide chain was converted to a cysteine (Cys). The change was confirmed by sequencing the mutant gene. Expression and nickel affinity purification of the wild type scFv and the C-terminal Cys containing mutant was confirmed by sodium dodecyl sulfate (SDS) polyacrylamide gel electrophoresis (PAGE), visualized with Coomassie blue stain at a molecular weight consistent with the scFv. Western blot analysis of the scFv SDS PAGE gel was performed with an anti-FLAG tag HRP conjugate. The Western blot analysis confirmed that the identity of the gel band was the scFv.

The scFv were clones modified with azide containing bifunctional linkers. The wild type scFv was modified with N-hydroxy-succinimide (NHS) ester-polyethylene glycol (PEG)$_4$-azide. Without wishing to be bound to any theory, modification of wild type scFv with NHS ester-PEG$_4$-azide results in the random incorporation of PEG$_4$-azide on to free amines on surface lysine residues. The C-terminal scFv Cys construct was conjugated with maleimide-PEG$_3$-azide for site specific PEG$_3$-azide introduction on to the Cys sulfhydryl. The scFv constructs were analyzed for azide incorporation by reaction with a Dibenzocyclooctyne (DBCO)-PEG-Cy5 fluorescent probe. Azides react with DBCOs via a metal free click chemistry reaction to form a covalent linkage. Unreacted DBCO-Cy5 dye was removed from the reaction mixtures by 40 kDa cutoff size exclusion spin columns. The successful introduction of an azide group on the surface of the scFvs was confirmed by visualizing the wild type and C-terminal Cys scFv-PEG-Cy5 fluorescent dye constructs using a BioRad Versa-Doc imager.

The azide conjugated scFv were then reacted with C dots containing 1-3 DBCOs on their surfaces. The reaction was allowed to continue for 12 h at room temperature. Unconjugated scFv was purified from conjugated scFv-C dots using multiple techniques including phosphate buffered saline washes in 50,000 molecular weight cut off spin columns, G-200 size exclusion column chromatography or size exclusion spin columns and velocity sedimentation thought a sucrose cushion. Velocity sedimentation and size exclusion chromatography appear to be the most scalable methods of purification. The purified scFv C-dot conjugates were analyzed by dot blot scFv immune-detection/particle fluorescence assays, gel electrophoresis and fluorescent ELISAs with immobilized MMP-12.

These methods can be applied to other types of antibody fragments, e.g., sdAbs.

FIG. 1 shows a schematic illustration showing the synthesis of $^{89}$Zr-labeled C'dot radioimmunoconjugate using a chelator-based radiolabeling technique. PEGylated and maleimide-functionalized C' dot (C' dot-PEG-Mal, 1) was first reacted with reduced glutathione (GSH) to introduce the —NH$_2$ groups for the following-up bioconjugates, forming C' dot-PEG-GSH (2). Then the nanoparticle was conjugated with DBCO-PEG4-NHS ester and DFO-NCS, forming C' dot-PEG-DBCO (3) and DFO-C' dot-PEG-DBCO (4), respectively. Azide-functionalized small targeting ligands, such as single-chain variable fragment (scFv-azide) (or single-domain antibody, sdAb-azide), was conjugated to the nanoparticle based on strain-promoted azide-alkyne cycloaddition, forming DFO-C' dot-PEG-scFv (5). The final C'dot radioimmunoconjugate ($^{89}$Zr-DFO-C' dot-PEG-scFv, 6) was by labeling it with $^{89}$Zr-oxalate. The schematic illustrated in FIG. 1 is not limited to scFv and can include various types of antibody fragments, e.g., sdAbs.

Figure 2A:
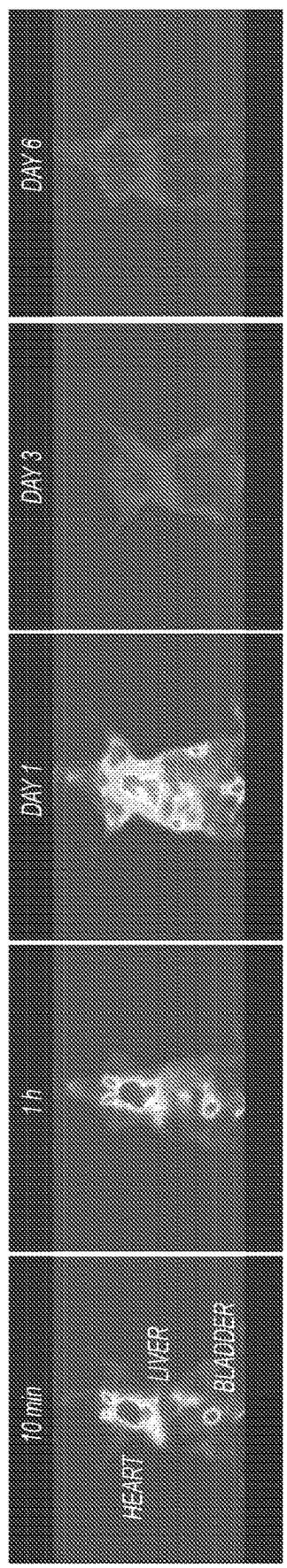
FIGS. 2A and 2B show in vivo (FIG. 2A) coronal and (FIG. 2B) sagittal PET images of $^{89}$Zr-DFO-C' dot-PEG at different post-injection time points (10 min, 1 h, Day 1, Day 3 and Day 6) in a healthy nude mouse. The reaction ratio between C' dot-PEG-Mal and GSH was kept at 1:20. The PET images were acquired by using a Focus 120 MicroPET scanner.
Figure 2B:
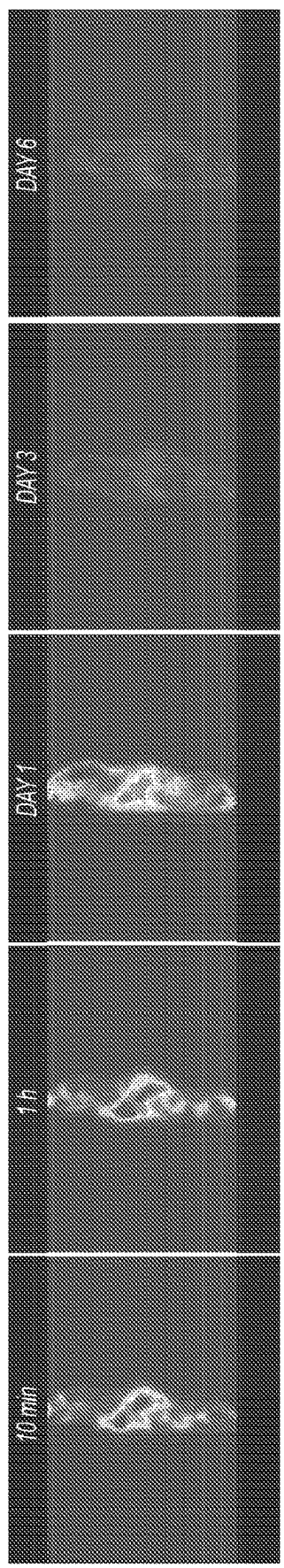

FIGS. 2A and 2B show in vivo (FIG. 2A) coronal and (FIG. 2B) sagittal PET images of $^{89}$Zr-DFO-C' dot-PEG at different post-injection time points (10 min, 1 h, Day 1, Day 3 and Day 6) in a healthy nude mouse. The reaction ratio between C' dot-PEG-Mal and GSH was kept at 1:20. The PET images were acquired by using a Focus 120 MicroPET scanner.

Figure 3:
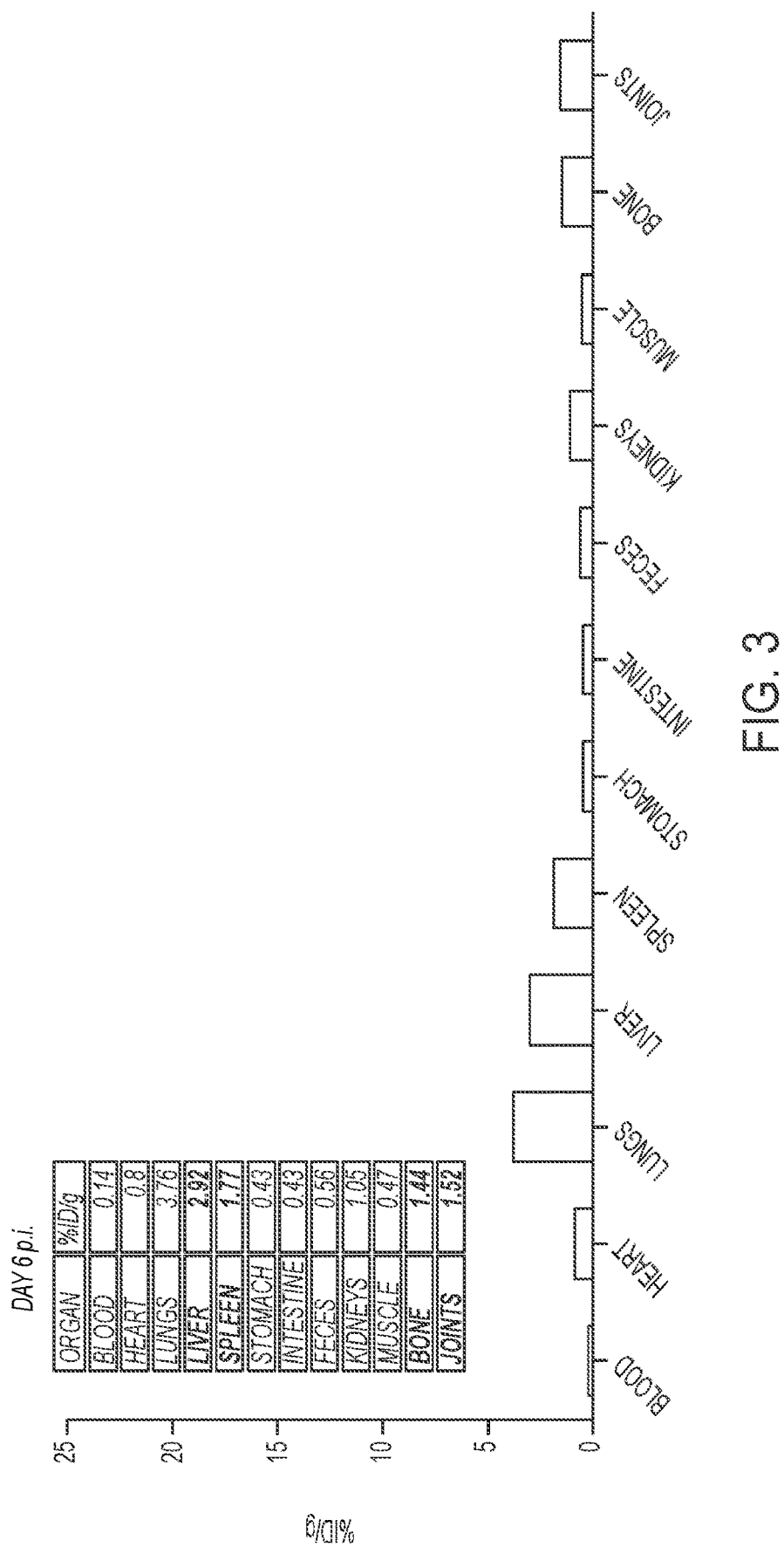
FIG. 3 shows biodistribution data of $^{89}$Zr-DFO-C' dot-PEG in a healthy nude mouse on Day 6. Less than 2% ID/g of bone (and joint) uptake was observed.

FIG. 3 shows biodistribution data of $^{89}$Zr-DFO-C' dot-PEG in a healthy nude mouse on Day 6. Less than 2% ID/g of bone (and joint) uptake was observed.

Figure 4B:
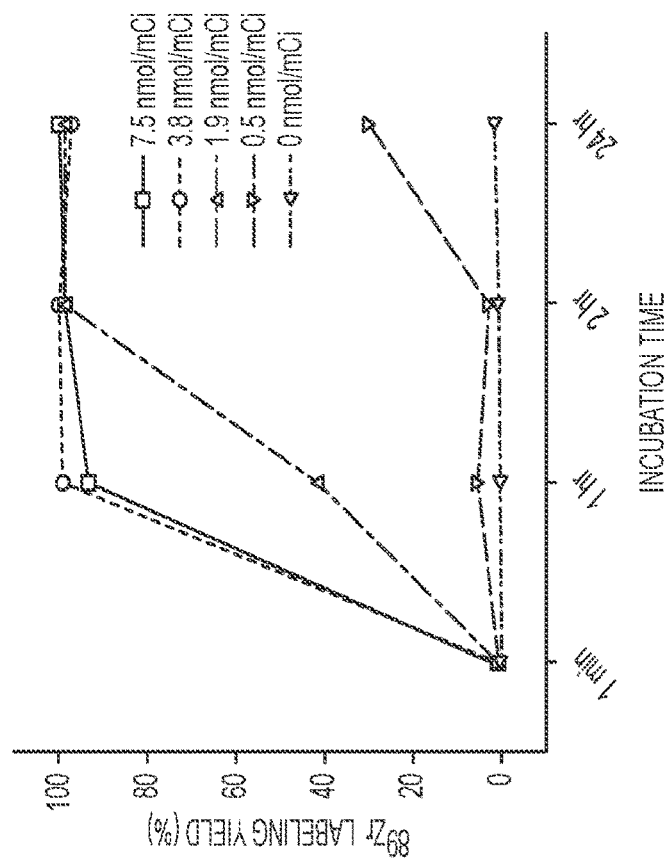
FIGS. 4A and 4B show a chelator-free $^{89}$Zr radiolabeling experimental example.
Figure 4A:
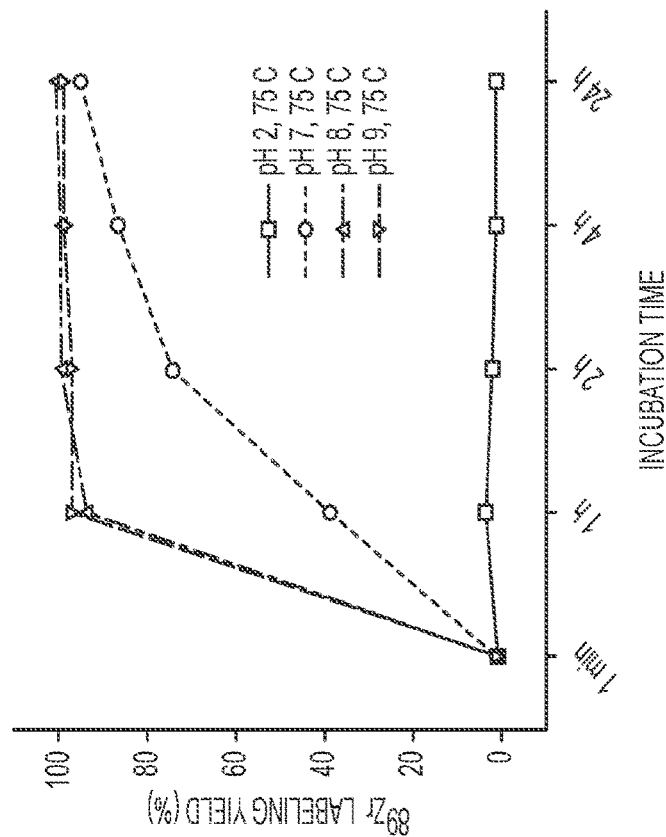

FIGS. 4A and 4B show a chelator-free $^{89}$Zr radiolabeling experimental example.

FIG. 4A shows $^{89}$Zr labeling yields of C' dot-PEG-Mal under varied pH conditions at 75° C.

FIG. 4B shows $^{89}$Zr labeling yields of C' dot-PEG-Mal using varied combinations of C' dot to $^{89}$Zr-oxalate ratio.

FIGS. 5A and 5B show in vivo coronal PET images of [89Zr]C' dot-PEG at different post-injection time points (10 min, Day 1, Day 3 and Day 6) in a healthy nude mouse. [$^{89}$Zr]C' dot-PEG was synthesized by using a chelator-free radiolabeling technique.

The PET images were acquired by using a Focus 120 MicroPET scanner.

FIG. 5A shows PET images acquired without EDTA (ethylenediaminetetraacetic acid).

FIG. 5B shows PET images acquired with EDTA

Figure 6:
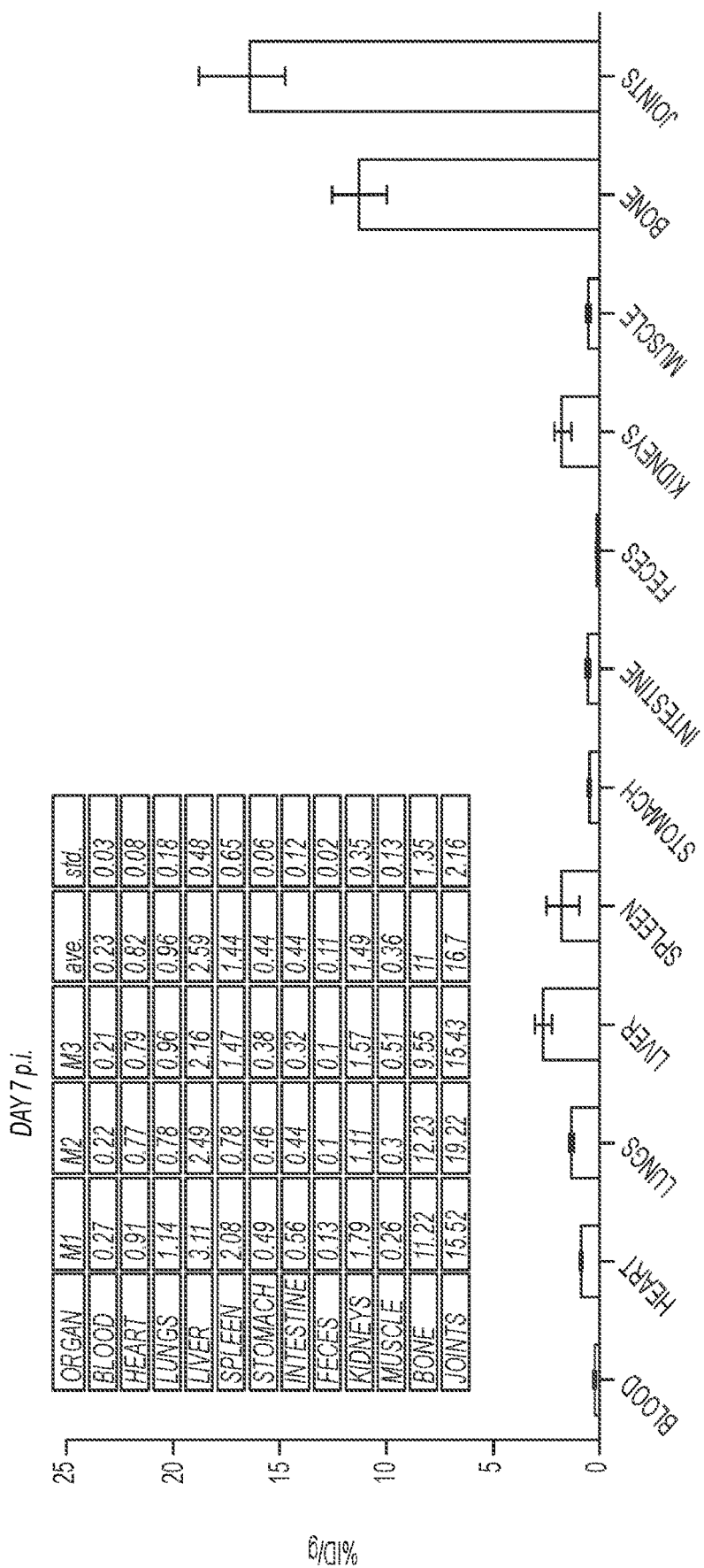
FIG. 6 shows biodistribution data of [$^{89}$Zr]C' dot-PEG in healthy nude mice (n=3) on Day 7. Over 10% ID/g of bone (and joint) uptake was observed in this case, indicating a less stable radiolabeling using a chelator-free method (when compared with that of chelator-based method).

FIG. 6 shows biodistribution data of [$^{89}$Zr]C' dot-PEG in healthy nude mice (n=3) on Day 7. Over 10% ID/g of bone (and joint) uptake (highlighted with a red box) was observed in this case, indicating a less stable radiolabeling using a chelator-free method (when compared with that of chelator-based method).

Figure 7:
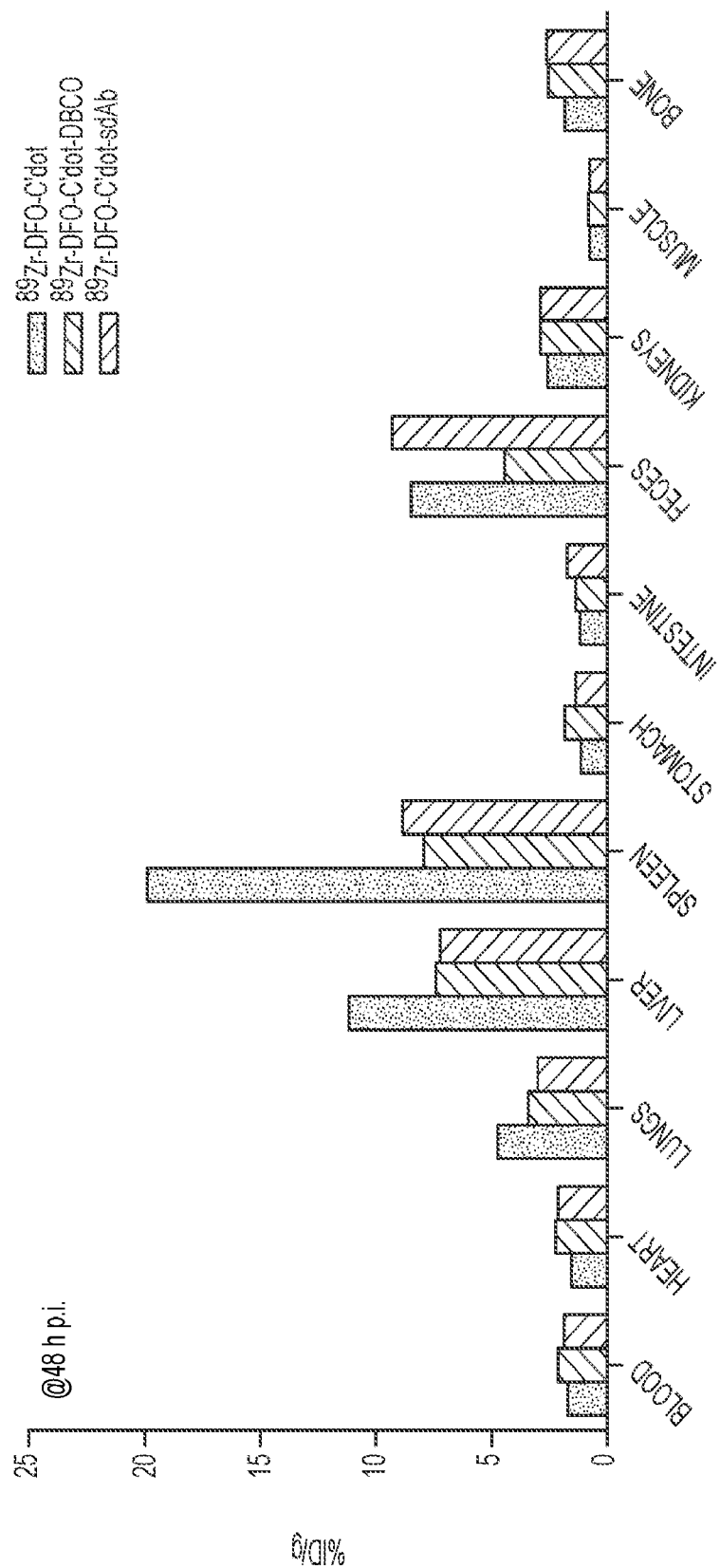
FIG. 7 shows biodistribution data of $^{89}$Zr-DFO-C' dot, $^{89}$Zr-DFO-C' dot-DBCO and $^{89}$Zr-DFO-C' dot-PEG-sdAb in healthy nude mice at 48 h post-injection. An improved pharmacokinetic profile (with prolonged blood circulation half-life and lower liver uptake) can be achieved by optimizing the number of DFO, DBCO and sdAb from each C' dot.

FIG. 7 shows biodistribution data of $^{89}$Zr-DFO-C' dot, $^{89}$Zr-DFO-C' dot-DBCO and $^{89}$Zr-DFO-C' dot-PEG-sdAb in healthy nude mice at 48 h post-injection. An improved pharmacokinetic profile (with prolonged blood circulation half-life and lower liver uptake) can be achieved by optimizing the number of DFO, DBCO and sdAb from each C' dot.

What is claimed is:

1. An immunoconjugate comprising:
    a nanoparticle coated with an organic polymer; and
    an antibody fragment conjugated to the organic polymer-coated nanoparticle,
    wherein the nanoparticle has a diameter no greater than 20 nanometers,
    wherein the nanoparticle comprises a silica-based core and a silica shell surrounding at least a portion of the core, and
    wherein the antibody fragment is a single chain variable fragment (scFv).

2. The immunoconjugate of claim 1, wherein the antibody fragment is covalently or non-covalently bonded to the nanoparticle via a linker or covalently or non-covalently bonded directly to the nanoparticle, or associated with the nanoparticle or a composition surrounding the nanoparticle.

3. The immunoconjugate of claim 1, wherein the antibody fragment is from about 25 kDa to about 30 kDa.

4. The immunoconjugate of claim 1, wherein the nanoparticle comprises a fluorescent compound within the core.

5. The immunoconjugate of claim 1, wherein the nanoparticle has from one to ten antibody fragments attached thereto.

6. The immunoconjugate of claim 1, wherein the nanoparticle has a diameter no greater than 15 nanometers.

7. The immunoconjugate of claim 1, wherein the nanoparticle has a diameter in a range from 1 nm to 20 nm.

8. The immunoconjugate of claim 1, wherein the antibody fragment comprises anti-VEGF-A.

9. The immunoconjugate of claim 1, wherein the immunoconjugate comprises one or more imaging agents.

10. The immunoconjugate of claim 9, wherein the one or more imaging agents comprise a PET tracer.

11. The immunoconjugate of claim 9, wherein the one or more imaging agents comprise a fluorophore.

12. The immunoconjugate of claim 1, further comprising a therapeutic agent.

13. The immunoconjugate of claim 12, wherein the therapeutic agent comprises a chemotherapy drug.

14. The immunoconjugate of claim 12, wherein the therapeutic agent comprises a radioisotope.

15. The immunoconjugate of claim 14, wherein the radioisotope is a member selected from the group consisting of $^{99m}$Tc, $^{111}$In, $^{64}$Cu, $^{67}$Ga, $^{186}$Re, $^{188}$Re, $^{153}$Sm, $^{177}$Lu, $^{67}$Cu, $^{123}$I, $^{124}$I, $^{125}$I, $^{11}$C, $^{13}$N, $^{15}$O, $^{18}$F, $^{186}$Re, $^{188}$Re, $^{153}$Sm, $^{166}$Ho, $^{177}$Lu, $^{149}$Pm, $^{90}$Y, $^{213}$Bi, $^{103}$Pd, $^{109}$Pd, $^{159}$Gd, $^{140}$La, $^{198}$Au, $^{199}$Au, $^{169}$Yb, $^{175}$Yb, $^{165}$Dy, $^{166}$Dy, $^{67}$Cu, $^{105}$Rh, $^{111}$Ag, $^{89}$Zr, $^{225}$Ac, and $^{192}$Ir.

16. The immunoconjugate of claim 1, wherein the immunoconjugate comprises a first chelator.

17. The immunoconjugate of claim 16, wherein the antibody fragment and the first chelator are conjugated to the organic polymer-coated nanoparticle via a click reactive group.

18. The immunoconjugate of claim 16, wherein the antibody fragment and the first chelator are conjugated to the organic polymer-coated nanoparticle via an amine.

19. The immunoconjugate of claim 1, wherein the nanoparticle has a diameter no greater than 10 nanometers.

20. The immunoconjugate of claim 13, wherein the chemotherapy drug is a member selected from the group consisting of sorafenib, paclitaxel, docetaxel, MEK162, etoposide, lapatinib, nilotinib, crizotinib, fulvestrant, vemurafenib, bexorotene, and camptotecin.

* * * * *